US010676490B2

(12) United States Patent
Dingra et al.

(10) Patent No.: US 10,676,490 B2
(45) Date of Patent: Jun. 9, 2020

(54) USE OF AMINE CARBOXYBORANES AS THERAPEUTIC DELIVERY OF CARBON MONOXIDE AND AS GENERAL DRUG DELIVERY SYSTEM IN THE PRESENCE OF REACTIVE OXYGEN SPECIES

(71) Applicants: University of Alaska Anchorage, Anchorage, AK (US); The Research Foundation for the State University of New York, Albany, NY (US); Florida Southwestern State College, Fort Myers, FL (US)

(72) Inventors: Nin N. Dingra, Fort Myers, FL (US); Theppawut Israsena Na Ayudhya, Fort Myers, FL (US)

(73) Assignees: Florida Southwestern State College, Fort Myers, FL (US); The Research Foundation for the State University of New York, New York, NY (US); University of Alaska Anchorage, Anchorage, AK (US)

( * ) Notice: Subject to any disclaimer, the term of this patent is extended or adjusted under 35 U.S.C. 154(b) by 4 days.

(21) Appl. No.: 15/742,463

(22) PCT Filed: Jul. 7, 2016

(86) PCT No.: PCT/US2016/041370
§ 371 (c)(1),
(2) Date: Jan. 5, 2018

(87) PCT Pub. No.: WO2017/007955
PCT Pub. Date: Jan. 12, 2017

(65) Prior Publication Data
US 2018/0194784 A1    Jul. 12, 2018

Related U.S. Application Data

(60) Provisional application No. 62/281,238, filed on Jan. 21, 2016, provisional application No. 62/189,249, filed on Jul. 7, 2015.

(51) Int. Cl.
*C07F 5/02* (2006.01)
*A61K 31/69* (2006.01)
*A61P 43/00* (2006.01)

(52) U.S. Cl.
CPC .............. *C07F 5/027* (2013.01); *A61K 31/69* (2013.01); *A61P 43/00* (2018.01)

(58) Field of Classification Search
CPC .................................................... C07F 5/027
See application file for complete search history.

(56) References Cited

U.S. PATENT DOCUMENTS

| | | |
|---|---|---|
| 3,773,919 A | 11/1973 | Boswell et al. |
| 4,312,989 A | 1/1982 | Spielvogel et al. |
| 4,485,045 A | 11/1984 | Regen |
| 4,544,545 A | 10/1985 | Ryan et al. |
| 4,619,794 A | 10/1986 | Hauser |
| 4,657,902 A | 4/1987 | Kappas et al. |
| 4,699,903 A | 10/1987 | Rideout et al. |
| 4,977,268 A * | 12/1990 | McPhail ............... C07F 5/027 548/110 |
| 5,362,732 A * | 11/1994 | Spielvogel ........... C07D 473/00 514/256 |
| 5,664,563 A | 9/1997 | Schroeder et al. |
| 5,888,982 A | 3/1999 | Perrella et al. |
| 5,981,689 A | 11/1999 | Mitchell et al. |
| 6,066,333 A | 5/2000 | Willis et al. |
| 7,045,140 B2 | 5/2006 | Motterlini et al. |
| 7,678,390 B2 | 3/2010 | Choi et al. |
| 8,236,339 B2 | 8/2012 | Motterlini et al. |
| 8,389,572 B2 | 3/2013 | Motterlini et al. |
| 9,163,044 B2 | 10/2015 | Blattler et al. |
| 2006/0127501 A1 | 6/2006 | Motterlini et al. |
| 2007/0059382 A1 | 3/2007 | Carper et al. |

FOREIGN PATENT DOCUMENTS

| | | |
|---|---|---|
| DE | 3218121 A1 | 11/1983 |
| EP | 0036676 A1 | 9/1981 |
| EP | 0052322 A2 | 5/1982 |
| EP | 0058481 A1 | 8/1982 |
| EP | 0088046 A2 | 9/1983 |
| EP | 0102324 A2 | 3/1984 |

(Continued)

OTHER PUBLICATIONS

Triethylamine, https://www.epa.gov/sites/production/files/2016-09/documents/triethylamine.pdf (Year: 2000).*
Dembitsky, V.M. et al., Synthesis and Biological Activity of α-aminoboronic Acids, Amine-Carboxyboranes and Their Derivatives. Tetrahedron. 2003; 59(5):579-93.
Eppstein, D.A. et al., Biological Activity of Liposome-Encapsulated Murine Interferon Gamma is Mediated by a Cell Membrane Receptor. Proc Natl Acad Sci USA. 1985; 82(11):3688-92.
Greene, T.W. and Wuts, P.G.M., Protecting Groups in Organic Synthesis. 2nd Ed. Wiley, New York, 1991.
Hwang, K.J. et al., Hepatic Uptake and Degradation of Unilamellar Sphingomyelin/Cholesterol Liposomes: A Kinetic Study. Proc Natl Acad Sci USA. 1980; 77(7):4030-4.

(Continued)

*Primary Examiner* — Joseph R Kosack
(74) *Attorney, Agent, or Firm* — Ballard Spahr LLP

(57) ABSTRACT

Disclosed is a method of delivering therapeutic carbon monoxide to the cells and tissues of a patient which comprises administering thereto a compound of the formula XBY1Y2C(O)V (I) or pharmaceutically acceptable salts thereof. In addition, disclosed is a method of delivering a drug to a diseased cell or tissue by administering a compound of formula I either wherein at least one of X is a drug containing an amino group or V is a drug containing an amino group or hydroxyl group less a hydrogen on the amino or hydroxyl group. Further disclosed are novel compounds of Formula I.

17 Claims, 20 Drawing Sheets

(56) References Cited

FOREIGN PATENT DOCUMENTS

| EP | 0133988 A2 | 3/1985 |
|---|---|---|
| EP | 0143949 A1 | 6/1985 |
| EP | 0336772 A2 | 10/1989 |
| WO | WO-93/05795 A1 | 4/1993 |
| WO | WO-93/09123 A1 | 5/1993 |
| WO | WO-01/25243 A1 | 4/2001 |
| WO | WO-03/066067 A2 | 8/2003 |
| WO | WO-2005/013691 A1 | 2/2005 |

OTHER PUBLICATIONS

Johnson, T.R. et al., Metal Carbonyls: A New Class of Pharmaceuticals? Angew Chem Int Ed Engl. 2003; 42(32):3722-9.

Langer, R. et al., Biocompatibility of Polymeric Delivery Systems for Macromolecules. J Biomed Mater Res. 1981; 15(2):267-77.

Langer, R. et al., Controlled Release of Macromolecules. ChemTech. 1982; 12:98-105.

Miller, M.C. et al., The Pharmacological Activities of the Metabolites of N-[(Trimethylamineboryl)-Carbonyl]-L-Phenylalanine Methyl Ester. Metal-Based D. 1996; 3(5):219-26.

Remington's Pharmaceutical Sciences. 17th Ed. Part 8. 1985, Mack Publishing Company, Easton, PA.

Sefton, M.V. et al., Ethylene-Vinyl Acetate Copolymer Microspheres for Controlled Release of Macromolecules. J Pharm Sci. 1984; 73(12):1859-61.

Sidman, U. et al., Controlled Release of Macromolecules and Pharmaceuticals from Synthetic Polypeptides Based on Glutamic Acid. Biopolymers. 1983; 22(1):547-56.

Spievogel et al., Boron Analogs of the a-Amino Acids. Synthesis, X-ray Crystal Structure, and Biological Activity of Ammonia-Carboxyborane, the Boron Analog of Glycine. J Am Chem Soc. 1980; 102(20):6343-4.

Supplementary European Search Report dated Nov. 28, 2018 by the European Patent Office for Patent Application No. 16821992.1, which was filed on Feb. 7, 2018 and published as EP 3319613 on May 16, 2018 (Inventor—Dingra et al.) (9 pages).

International Search Report and Written Opinion dated Sep. 26, 2016 by the International Searching Authority for Patent Application No. PCT/US2016/041370, which was filed on Jul. 7, 2016 and published as WO 2017/007955 on Jan. 12, 2017 (Inventor—Dingra et al.) (8 pages).

International Preliminary Report dated Jan. 9, 2018 by the International Searching Authority for Patent Application No. PCT/US2016/041370, which was filed on Jul. 7, 2016 and published as WO 2017/007955 on Jan. 12, 2017 (Inventor—Dingra et al.) (6 pages).

\* cited by examiner

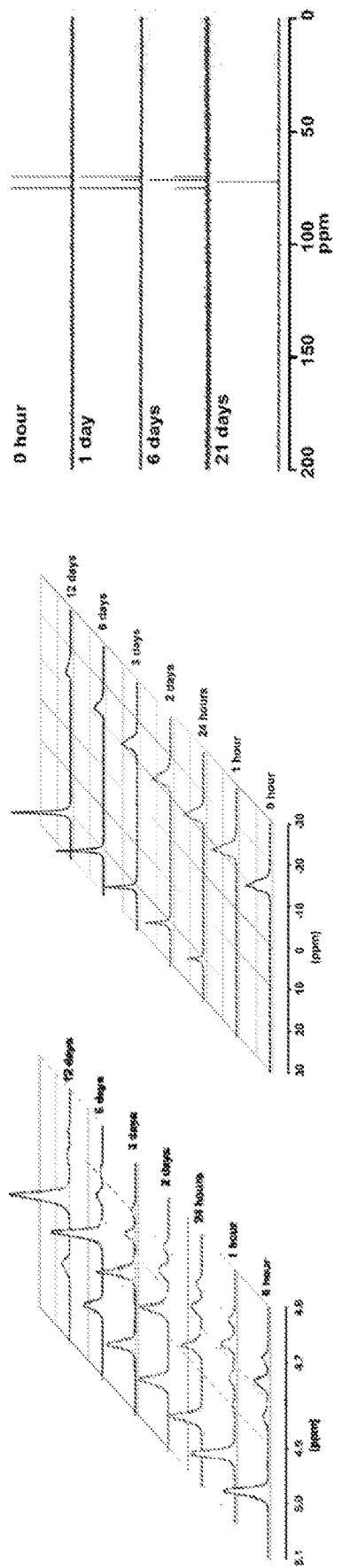
Figure 1. An example of monitoring CORCB decomposition by NMR spectroscopy. (A) Auto-decomposition of CORCB-1 as evident by $^1$H NMR. (B) Overlaid $^{11}$B NMR spectra showing progress of decomposition. (C) Overlaid $^{13}$C NMR spectra over a period of time.

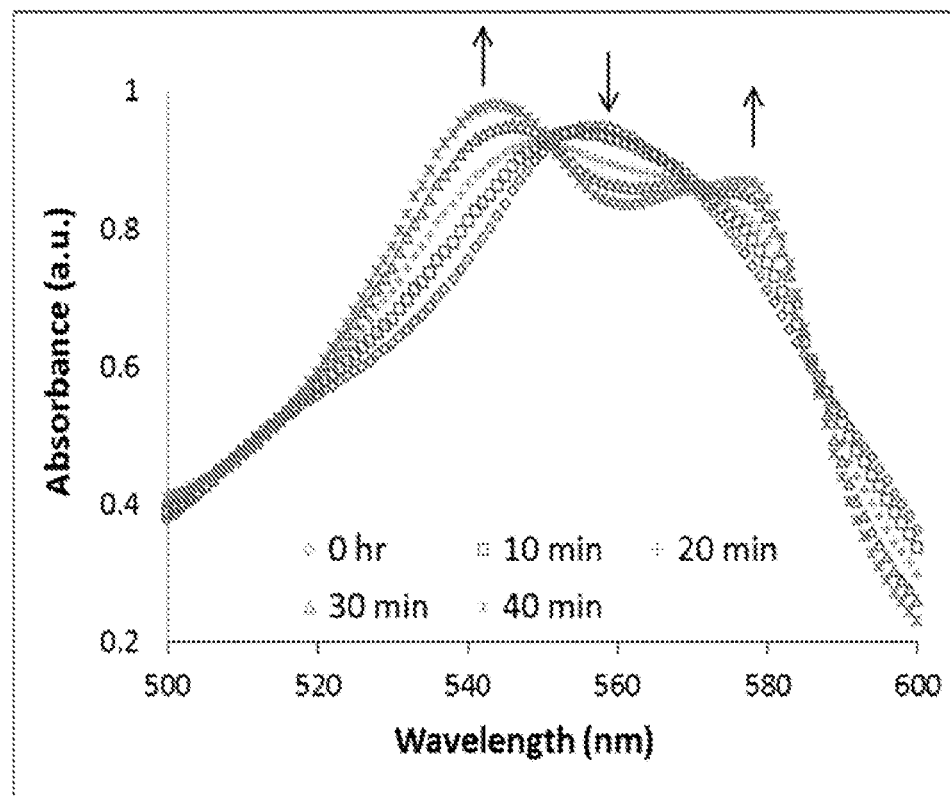
Figure 2. CO releasing property of CORCB-1 tested by traditional Mb assay. Upon incubation of deoxymyoglobin with CORCB-1 at 37 °C, UV-visible spectra were collected at different time points. Deoxymyoglobin gradually turns to carboxymyoglobin in a sealed cuvette.

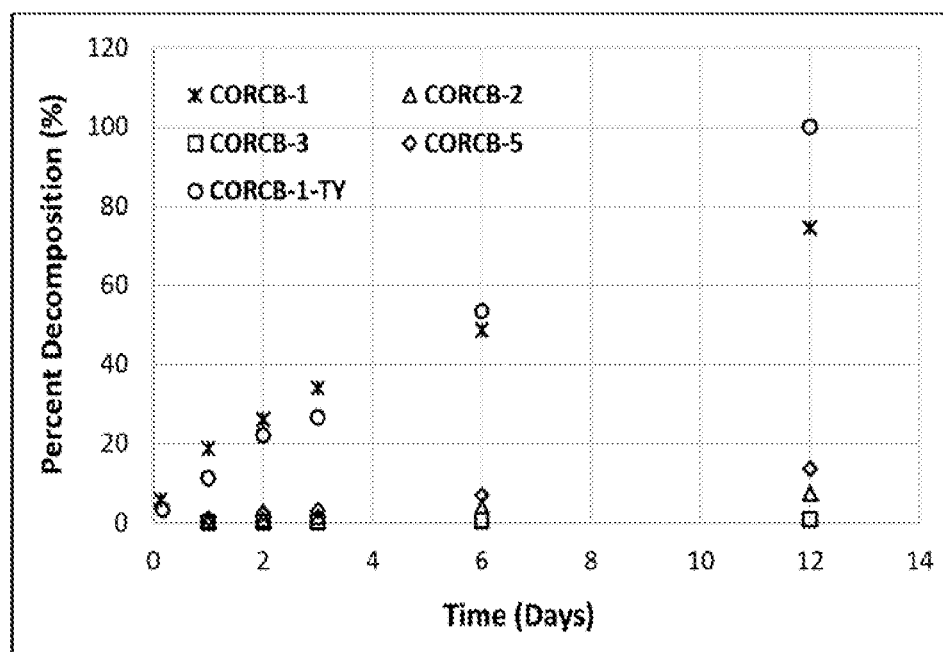
Figure 3. Auto-decomposition of CORCB acid forms monitored by $^1$H NMR. CORCBs were dissolved in $D_2O$ and incubated at 37°C. NMR spectra were taken at specified times to track the decomposition rates.

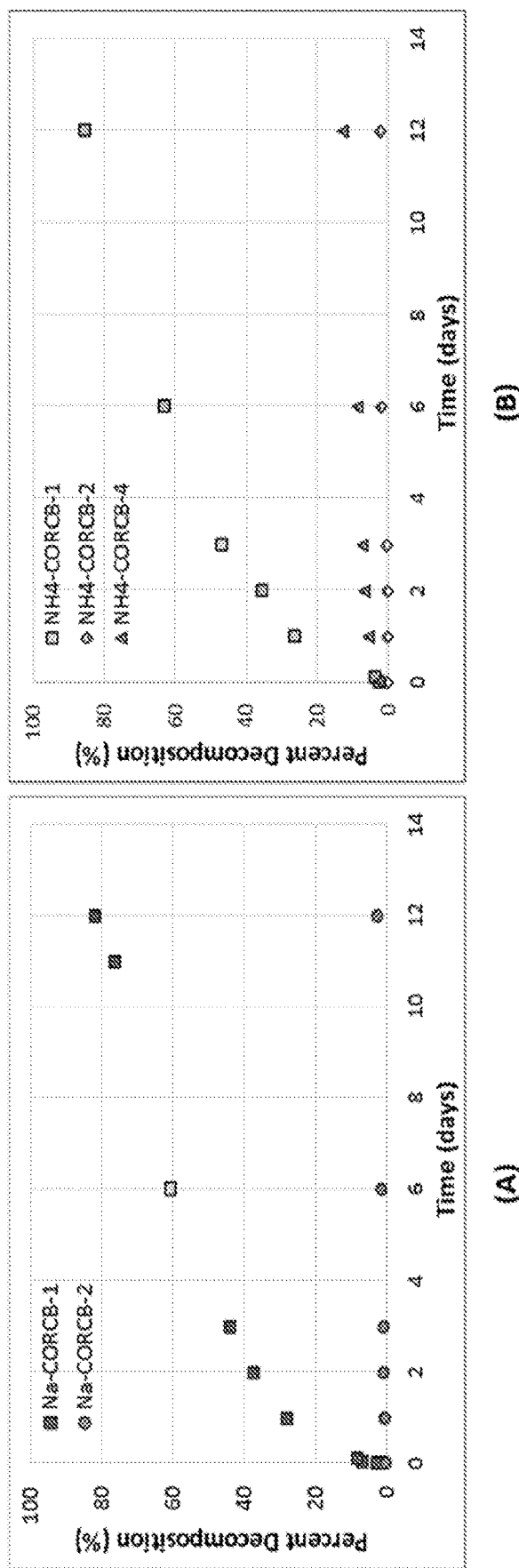
Figure 4. Auto-decomposition of CORCB salts monitored by ¹H NMR. (A) CORCB sodium salts and (B) CORCB ammonium salts. All CORCB salts are soluble in D₂O solvent. After incubation at 37°C, ¹H NMR spectra were taken at specified times to track the decomposition rates. Sodium salts of CORCB-3, 4, and 5 had insignificant amounts of decomposition, therefore data not shown.

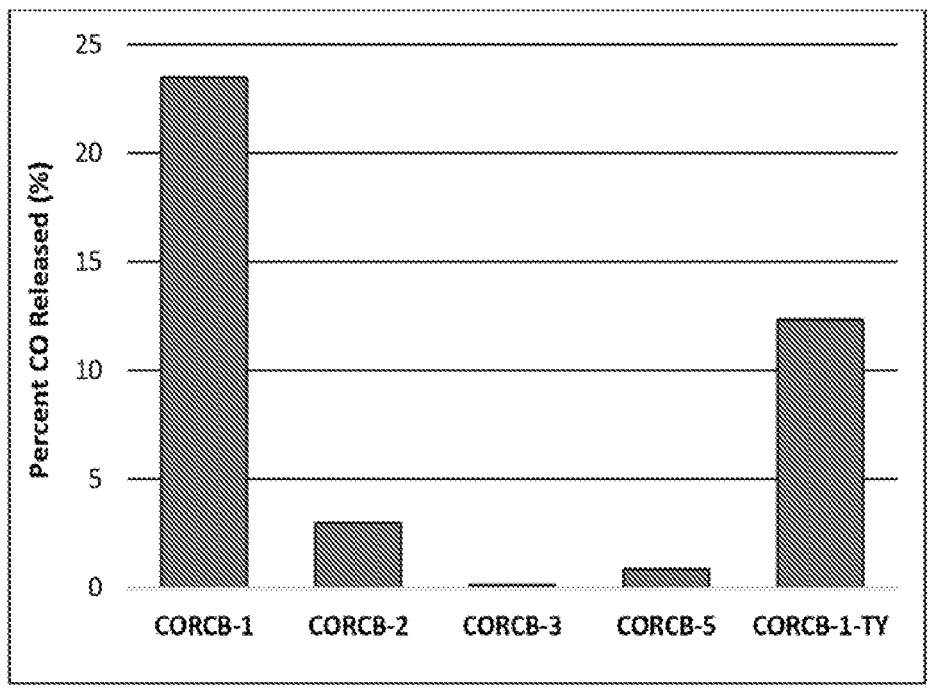
Figure 5. Percent CO released by CORCB acid forms measured with CO meter. CORCBs were dissolved in $H_2O$ and incubated at 37°C for 24 hours. The head space air that contained CO gas is analyzed by CO meter and the ppm readings converted to the micromole amount for percent calculation.

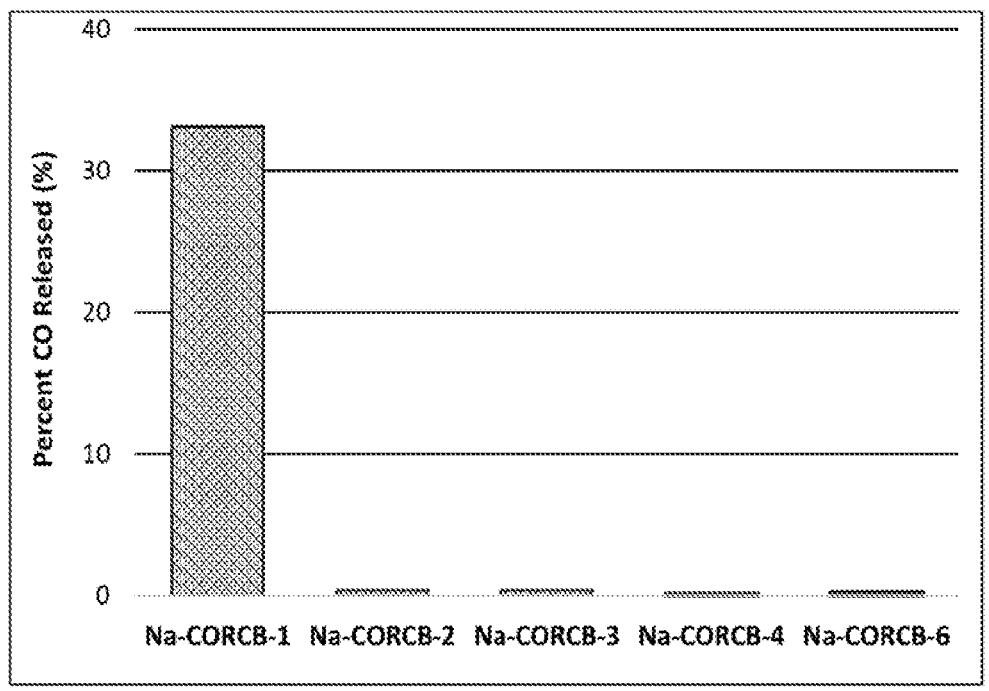
Figure 6. Percent CO released by sodium salts of CORCBs measured with CO meter. CORCB sodium salts were dissolved in $H_2O$ and incubated at 37°C for 24 hours. The head space air that contained CO gas is analyzed by CO meter and the ppm readings converted to the micromole amount for percent calculation.

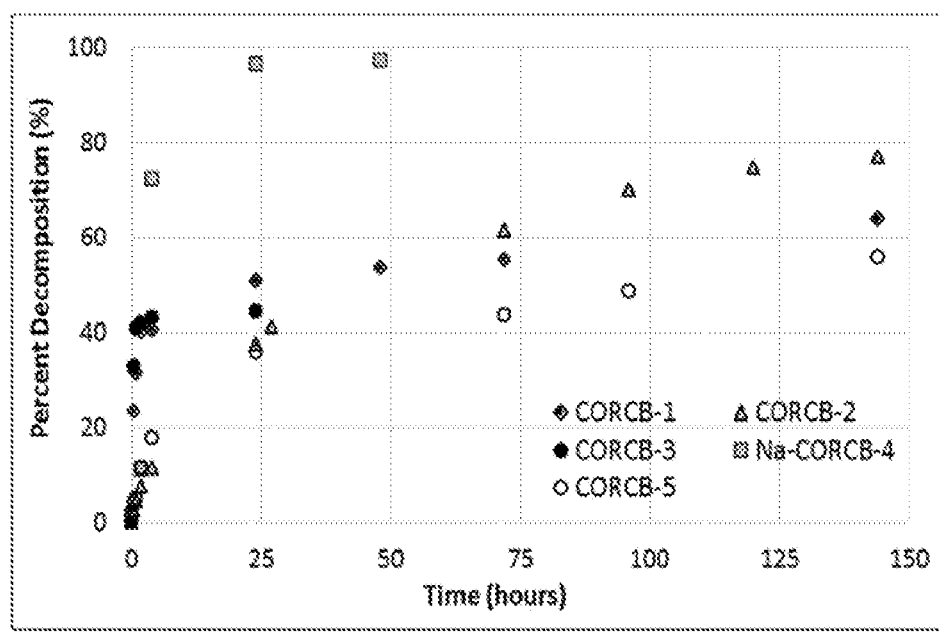
Figure 7. Percent decomposition of CORCBs in the presence of ROS monitored by $^1$H NMR. CORCBs were dissolved in $H_2O$ and 1.5 equivalents of $H_2O_2$ added before incubation in 37°C. $^1$H NMR spectra were taken at specified times to track the decomposition rates.

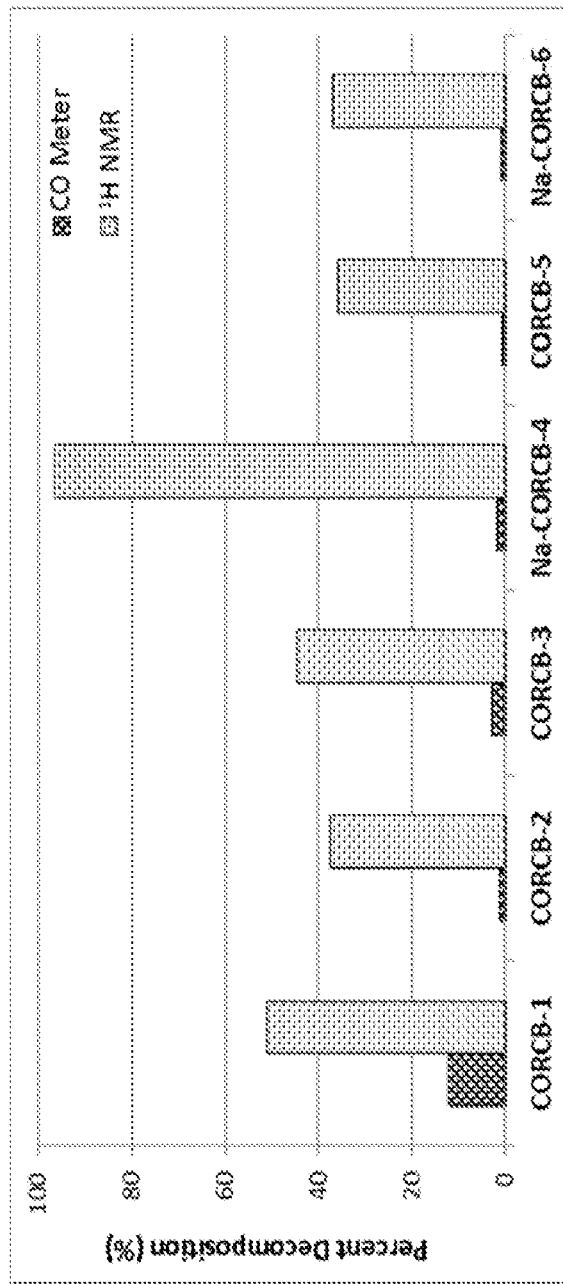

Figure 8. A comparison of percent decomposition of CORCBs in the presence of ROS monitored by $^1$H NMR and CO meter. CORCBs were dissolved in H$_2$O and 1.5 equivalents of H$_2$O$_2$ added before incubation at 37 °C for 24 hours. Measurements were taken and percent calculated. CO meter readings represent the amount of CO released and $^1$H NMR correspond to the amine group (or drug molecule) releasing property.

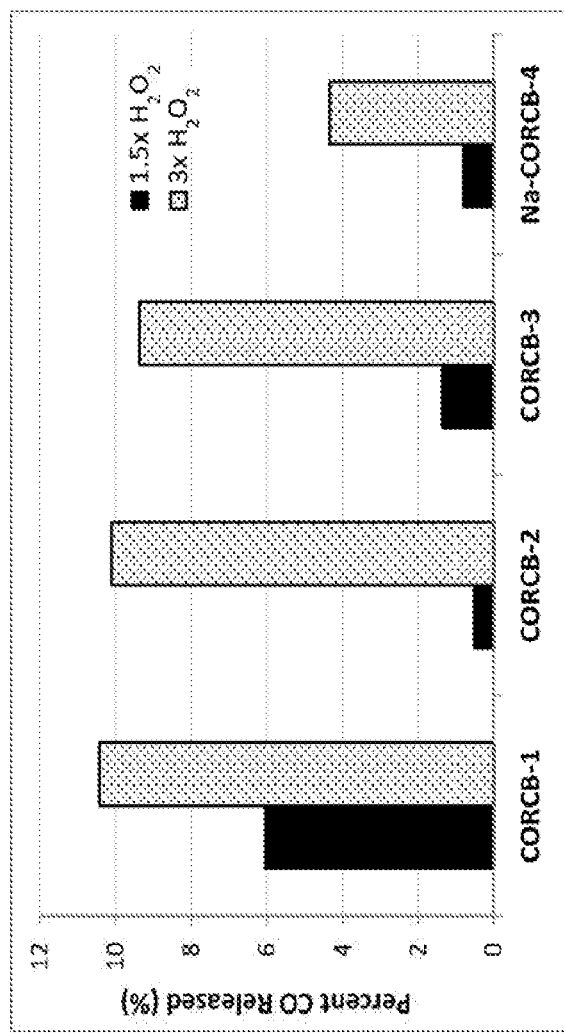
Figure 9. CO measurements using CO meter from CORCBs in the presence of 1.5 and 3 equivalents of ROS. CORCBs were incubated with respective amounts of $H_2O_2$ for 12 hours at 37 °C, and the CO concentration measured by CO meter.

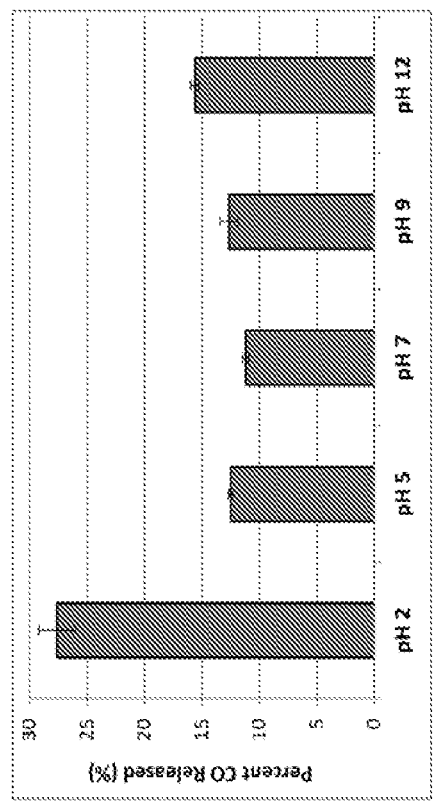
Figure 10. Percent CO generated by CORCB-1 in different pH monitored by CO meter. CORCB-1 was dissolved in H₂O with adjusted pH before incubation in 37°C. After 12 hours, CO gas in the head space was analyzed by CO meter.

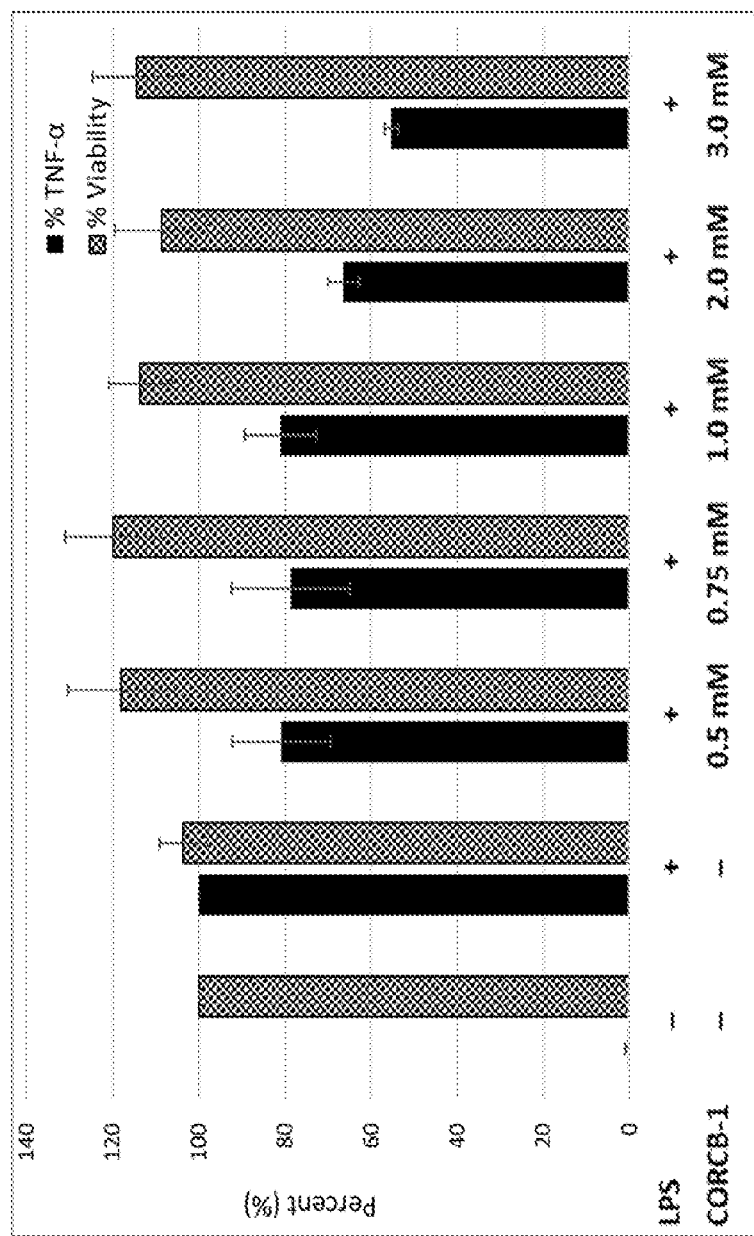
Figure 11. Anti-inflammatory and cell toxicity effect of CORCB-1 tested on mouse macrophages. LPS induced TNF-α production was tested first and cell viability assay was performed on the same cells. Untreated cells sample was set at 100% for calculating % viability and sample treated with only LPS was normalized to 100% for calculating TNF-α percentage.

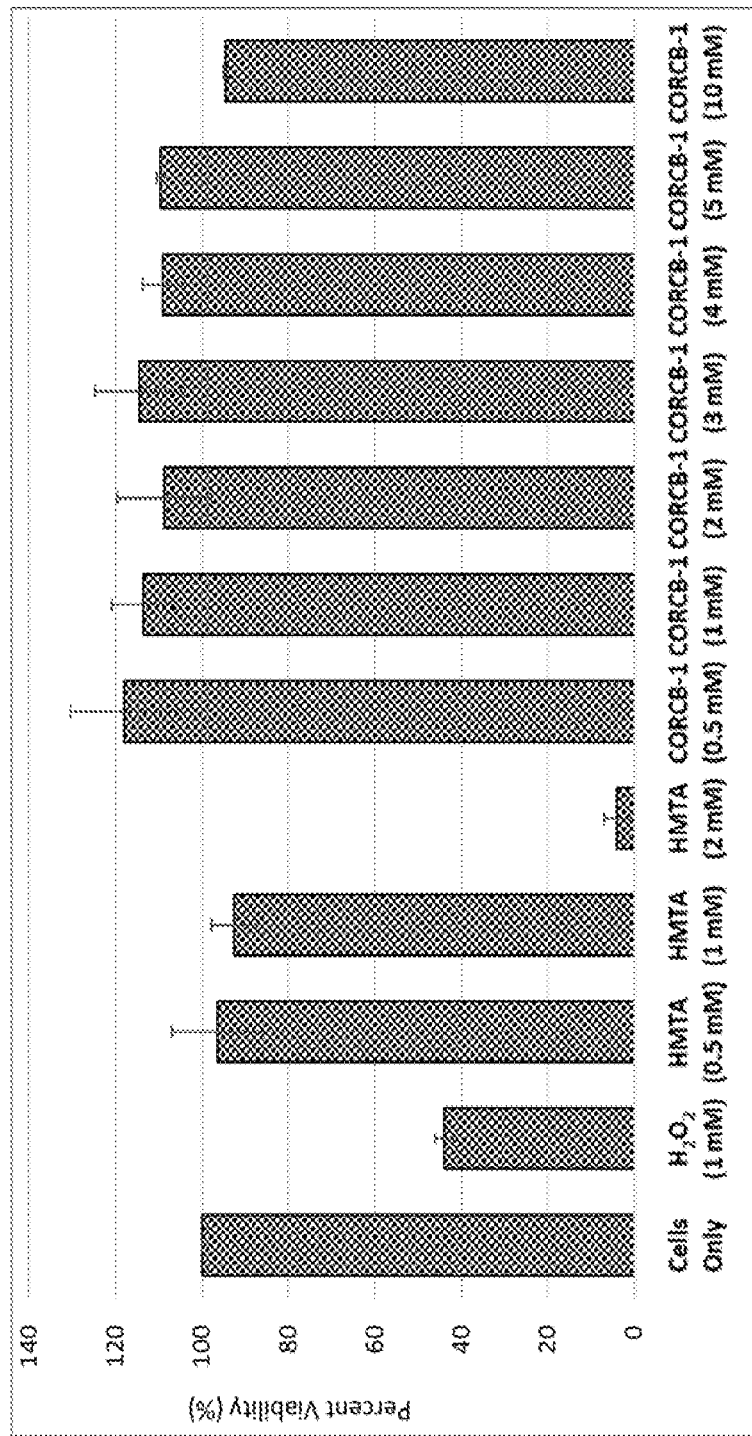
Figure 12. Cell toxicity of CORCB-1 tested on mouse macrophages. Data was normalized by cells only as 100%. Different concentrations of CORCB-1 was incubated with the cells for 24 hours and CellTiter Blue reagent was added to assess the viability.

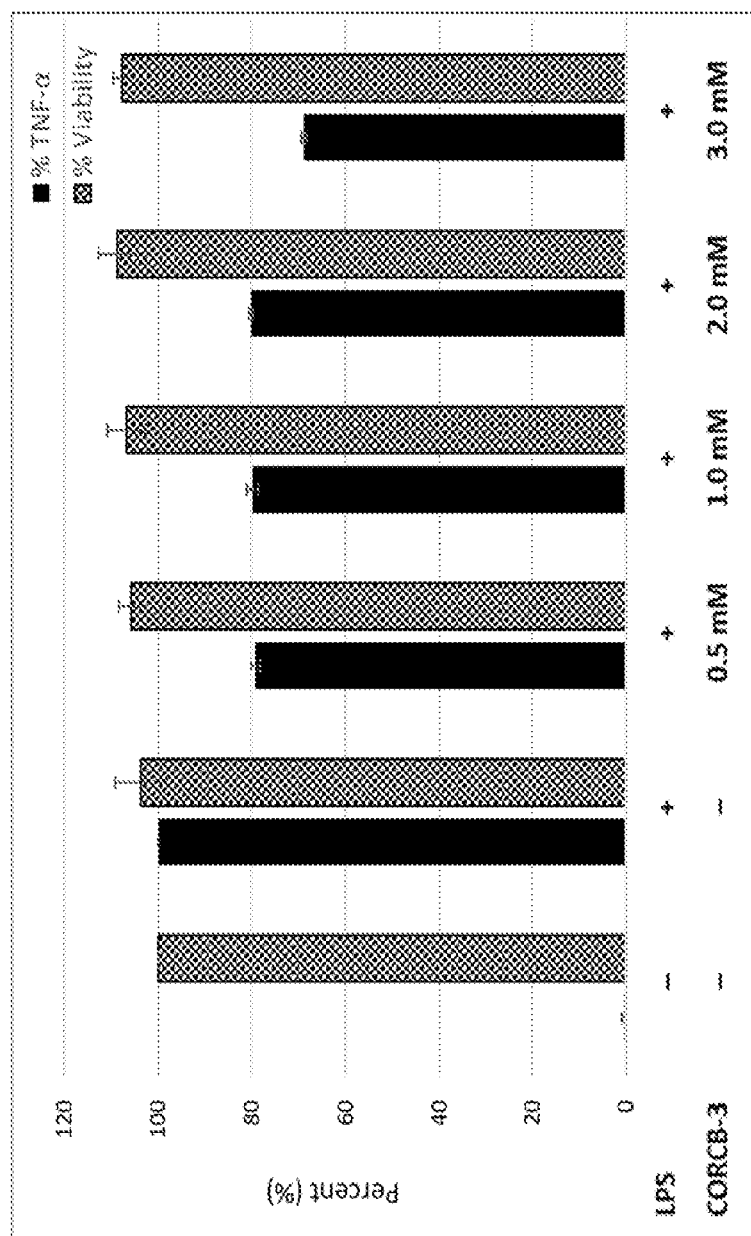
Figure 13. Anti-inflammatory and cell toxicity effect of CORCB-3 tested on mouse macrophages. LPS induced TNF-α production was tested first and cell viability assay was performed on the same cells. Untreated cells sample was set at 100% for calculating % viability and sample treated with only LPS was normalized to 100% for calculating TNF-α percentage.

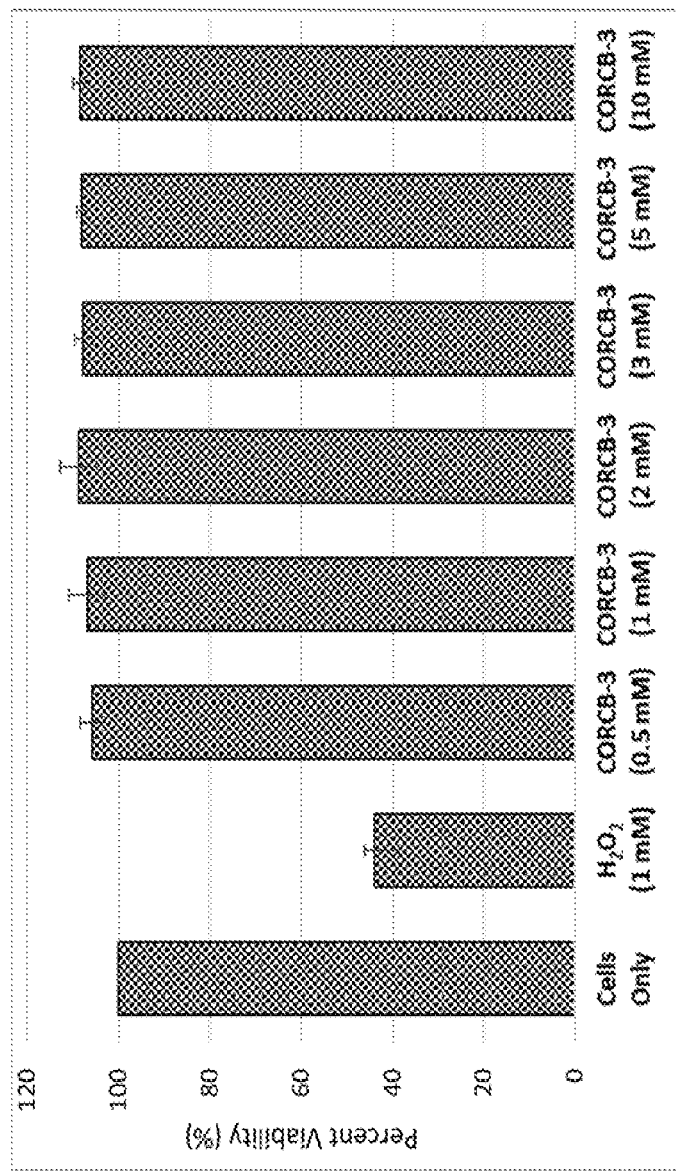
Figure 14. Cell toxicity of CORCB-3 tested on mouse macrophages. Data was normalized by cells only as 100%. Different concentrations of CORCB-3 was incubated with the cells for 24 hours and CellTiter Blue reagent was added to assess the viability.

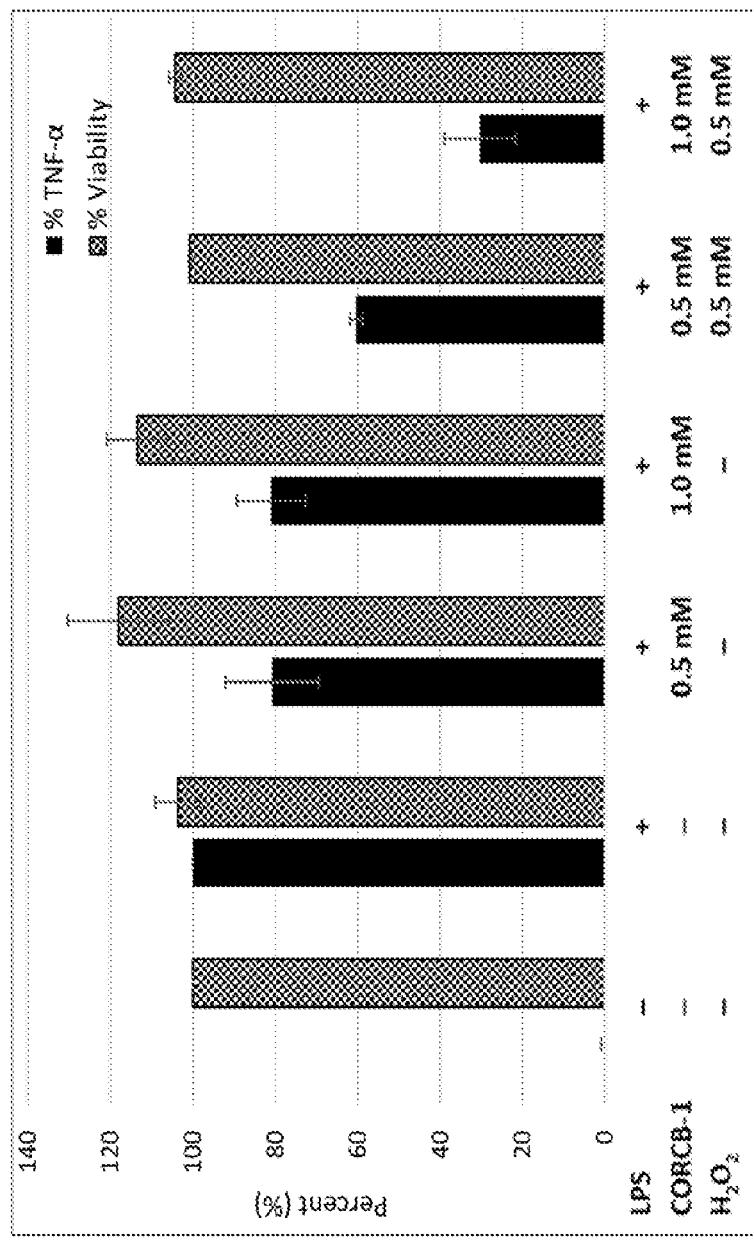

Figure 15. Anti-inflammatory and cell toxicity effect of CORCB-1 in the presence of hydrogen peroxide tested on mouse macrophages. LPS induced TNF-α production was tested first and cell viability assay was performed on the same cells. Untreated cells sample was set at 100% for calculating % viability and LPS only sample was normalized to 100% for calculating TNF-α percentage.

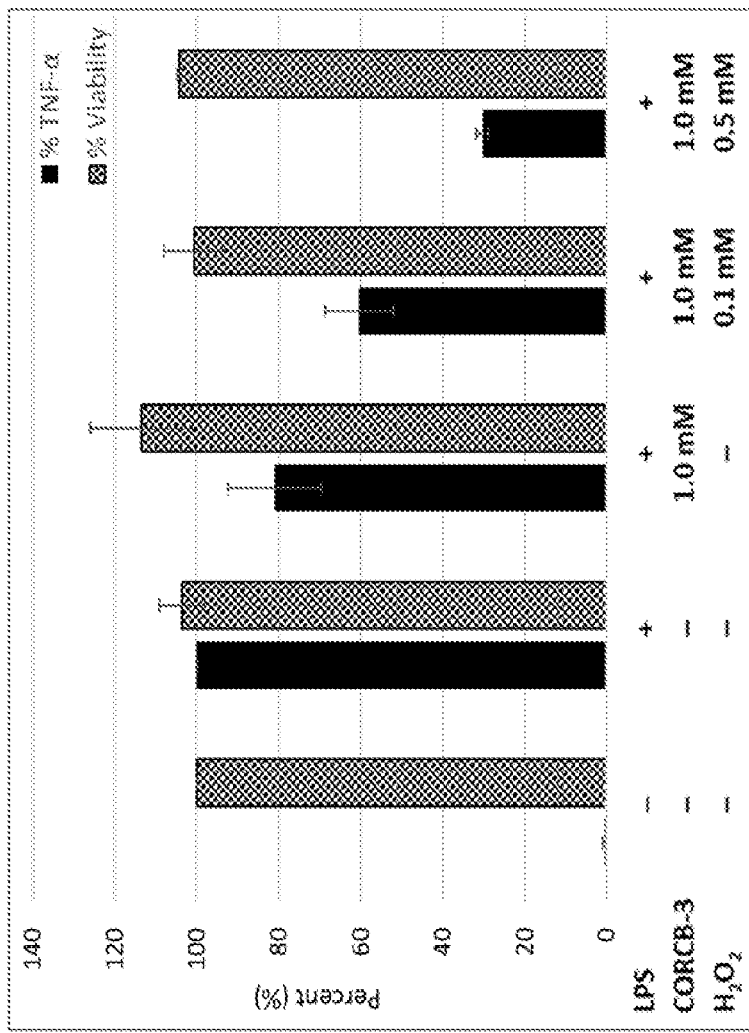

Figure 16. Anti-inflammatory and cell toxicity effect of CORCB-3 in the presence of hydrogen peroxide tested on mouse macrophages. LPS induced TNF-α production was tested first and cell viability assay was performed on the same cells. Untreated cells sample was set at 100% for calculating % viability and LPS only sample was normalized to 100% for calculating TNF-α percentage.

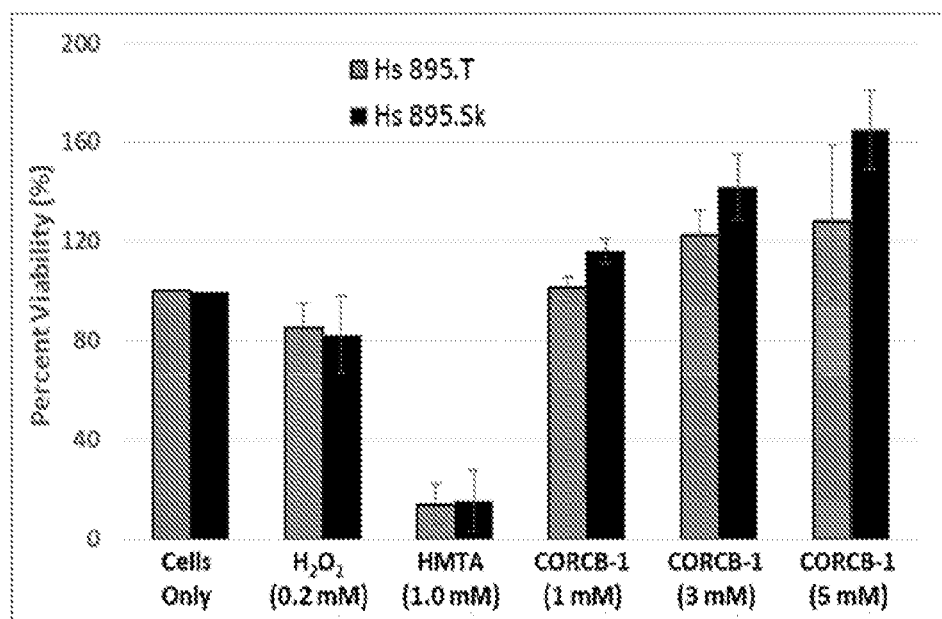
Figure 17. Cell growth enhancement of CORCB-1 tested on tumor cells (Hs 895.T) and normal cells (Hs 895.Sk). Data was normalized by setting untreated cells (cells only) as 100%. Different concentrations of CORCB-1 was incubated with the cells for 48 hours and CellTiter Blue reagent was added to assess the viability.

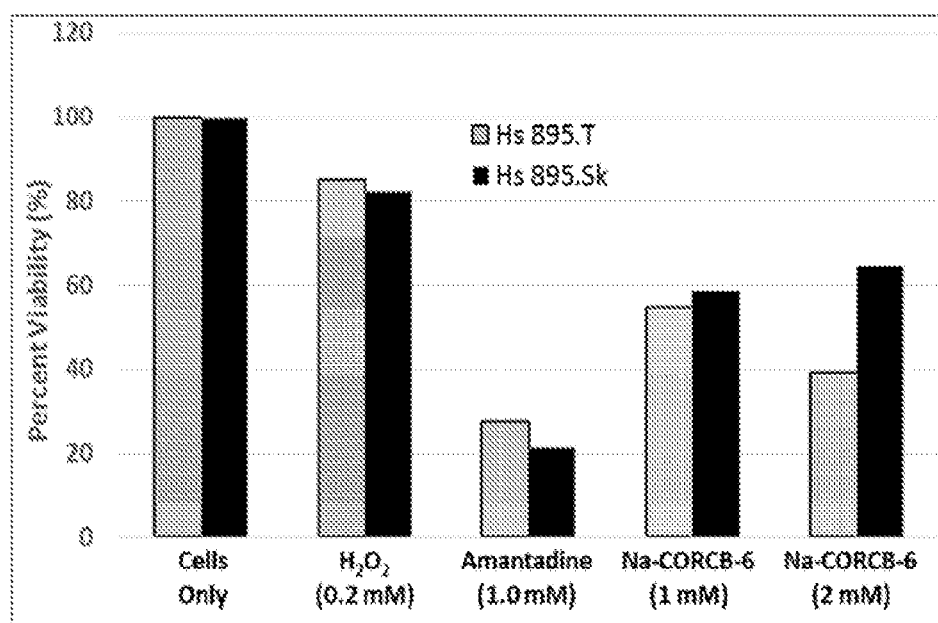
Figure 18. Effect of CORCB-6 on tumor cells (Hs 895.T) and normal cells (Hs 895.Sk). Data was normalized by setting untreated cells (cells only) as 100%. Different concentrations of CORCB-1 was incubated with the cells for 48 hours and CellTiter Blue reagent was added to assess the viability.

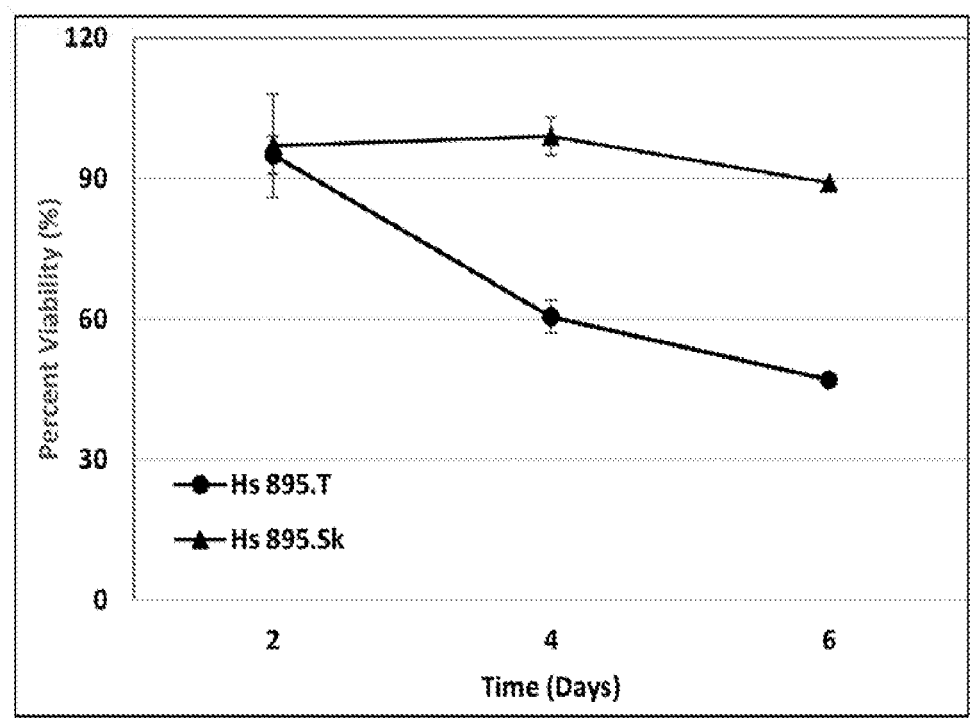
Figure 19. Anti-tumor activity of CORCB-1 in the presence of ROS. Fibroblast tumor cells (Hs 895.T) and normal cells (Hs 895.Sk) were treated with CORCB-1 (1 mM) in combination with $H_2O_2$ (0.2 mM). Cell viability was tested on 2, 4, and 6 days using CellTiter Blue reagent. Data was normalized by setting untreated cells as 100%.

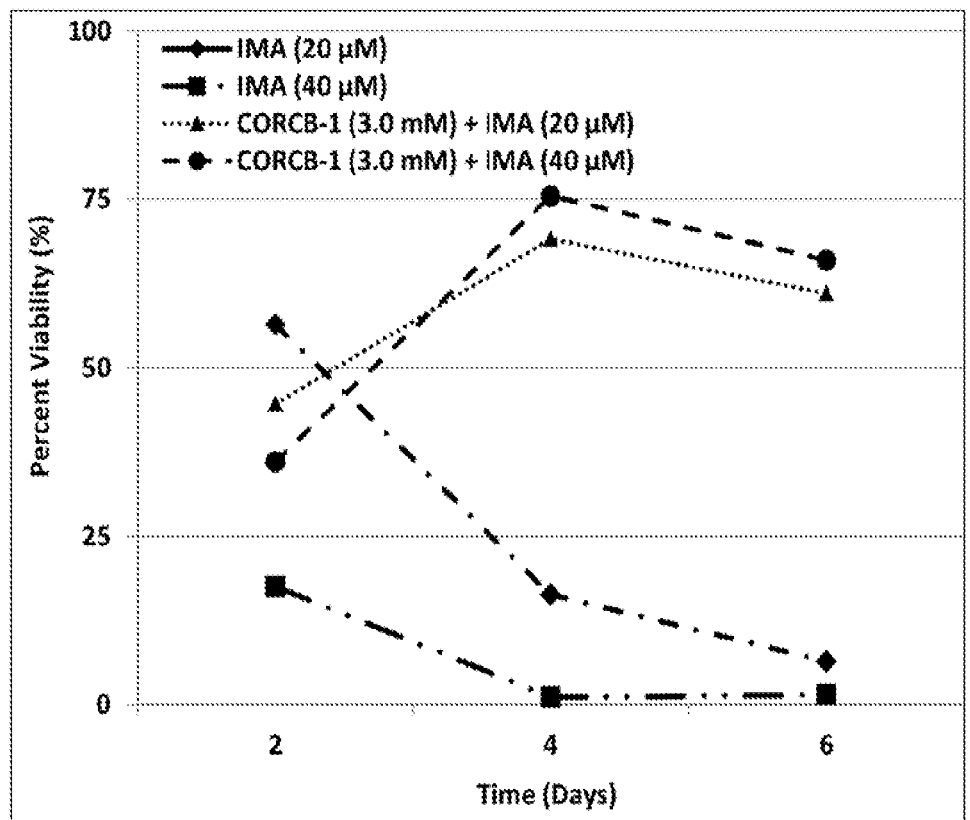

Figure 20. Cell rescue by CORCB-1 in the presence of toxic drugs such as imatinib used in chemotherapy. As controls, skin fibroblast cells (Hs 895.Sk) were treated with 20 and 40 µM concentrations of imatinib. Into two other samples containing 20 and 40 µM imatinib, CORCB-1 (3 mM) was added. Cell viability was tested on 2, 4 and 6 days using CellTiter Blue reagent. Data was normalized by setting untreated cells as 100%.

USE OF AMINE CARBOXYBORANES AS THERAPEUTIC DELIVERY OF CARBON MONOXIDE AND AS GENERAL DRUG DELIVERY SYSTEM IN THE PRESENCE OF REACTIVE OXYGEN SPECIES

RELATED APPLICATION

The present application is a national phase filing under 35 U.S.C. § 371 of International Application No. PCT/US2016/041370, filed on Jul. 7, 2016, which claims priority to U.S. provisional application U.S. Ser. No. 62/189,249, filed on Jul. 7, 2015, and U.S. Ser. No. 62/281,238, filed on Jan. 21, 2016, the content of which are incorporated by reference in their entireties.

BACKGROUND OF THE DISCLOSURE

Carbon monoxide (CO), a diatomic, colorless gas, has been shown to cause vasodilation, alleviate inflammatory responses, and provide graft survival during organ transplant. Endogenous CO is mainly produced by hemeoxygenases known as HO-1, HO-2, and HO-3 by catabolizing free heme. HO-2 is constitutively expressed in all cell types and may serve as a heme sensor as well as a regulatory factor for heme-responsive genes. An inducible isoform, HO-1, is affected by the external stimuli. Based on this knowledge, HO-1 knockouts mice are used in studying the beneficial effects of CO. Studies have shown that inhalation of CO rescued the HO-1 deficient mice from ischemic lung injury. HO-1 expression or its product CO demonstrated inhibition of vasoconstriction through the pathway independent of nitric oxide.

The anti-inflammatory effect of CO has been reported before by studying the endotoxin induced inflammatory responses. Lipopolysaccharides (LPS) from gram-negative bacterial cell wall were used as an inducer of inflammation in the HO-1 knockout animal models. Administering CO at low concentrations inhibited the LPS induced production of pro-inflammatory cytokines and tumor necrosis factor-$\alpha$ (TNF-$\alpha$) while increasing the production of anti-inflammatory cytokine interleukin 10.

The CO anti-inflammatory effect can be seen not only in the animal models but also in cell cultures in vitro. Murine macrophages have been used in various studies to show the effects of CO releasing molecules (CORMs). Specifically, RAW264.7 cells are used for producing inflammatory cytokines by introducing lipopolysaccharides (LPS) from *E. coli*. The anti-inflammatory effect of CO produced from CORMs can be detected by observing the reduced amount of inflammatory cytokines.

Hemeoxygenases are potential targets for drugs in alleviating various disorders. In cases where reduced heme catabolism is desired such as neonatal hyperbilirubinemia and anemias, hemeoxygenases can be inhibited to prevent the release of iron and bilirubin. (U.S. Pat. Nos. 4,657,902, 4,699,903, 5,888,982) Another practice is to produce CO endogenously in treatment desired for the effects of CO. Hemeoxygenase inducers such as prostaglandins, vitamin B12, hemin derivatives, and compounds that decrease nitric oxide synthesis described in U.S. Pat. Nos. 6,066,333 and 5,891,689 may increase HO activity by inducing HO-1 expression. The problem with inducing HO-1 activity for the benefit of generating CO is that it also produces the two potentially toxic byproducts, bilirubin and iron.

The effect of CO can be obtained alternatively by administering CO gas as described in U.S. Pat. No. 5,664,563 or applying locally to organs before transplantation. Although the beneficial effects can be seen in much lower CO concentrations than that used in human pulmonary function tests, the CO gas inhalation as a therapy is not desirable since the danger may outweigh the benefits if it is not conducted under controlled conditions.

Carbon monoxide is the most commonly encountered environmental poison. Administration of carbon monoxide by inhalation is thus not practical for clinical applications, as it requires special delivery devices such as ventilators, face masks, tents, or portable inhalers. Moreover, carbon monoxide delivery to therapeutic targets by inhalation is inefficient, because it involves transport of carbon monoxide by hemoglobin. Hemoglobin binds carbon monoxide reversibly, but with very high affinity. Therefore, the doses required to deliver carbon monoxide to therapeutic targets in diseased tissues are likely to be associated with adverse effects.

Carbon monoxide releasing molecules (CORMs), however, is a potential therapeutic alternative that can deliver carbon monoxide directly to therapeutic targets without the formation of intermediate CO-hemoglobin complexes (see, e.g., Johnson et al., *Angew Chem Int Ed Engl* (2003) 42:3722-3729). These molecules can release CO inside the body system or the cells to bypass the inhalation process. The advantages of carbon monoxide delivery by CORMs over carbon monoxide delivery by inhalation are generally recognized. A few examples of CORMs include the molecules discussed in U.S. Pat. Nos. 9,163,044; 8,389,572; 8,236,339; 7,678,390; and 7,045,140.

However, CORMs need to be able to deliver carbon monoxide selectively to diseased tissues. The identification of CORMs that are best suited for the treatment of a particular disease remains a major challenge of CORM development. Thus, there continues to remain a need for CORMs which, upon administration in vivo, selectively target a particular disease or organ with therapeutic benefit.

SUMMARY OF THE DISCLOSURE

An aspect of the present disclosure is directed to pharmaceutical compounds that release carbon monoxide in vivo. These carbon monoxide releasing compounds are amine carboxyboranes (CORCBs), which are biocompatible and have potential to be used for providing protection from damaging agents and targeted release of various drugs in diseased cells with elevated levels of ROS. More specifically, these amine carboxyboranes that deliver CO in a physiological condition have the formula:

   I or pharmaceutically acceptable salts,
where
each Y1 and Y2 may be the same or is different and is independently H, alkyl, halo, CN or C(O)V1;
V is O⁻, OR1 or NR1R2 or is a first drug, which drug has an amino group or an hydroxyl thereon in which a hydrogen atom of the hydroxyl or amine is not present;
V1 is O⁻, OR10 or NR10R12 or is a third drug, which drug has an amino group or a hydroxyl thereon in which a hydrogen atom of the hydroxyl or amine is not present;
R1, R2, R10 and R12 are independently hydrogen, lower alkyl, aryl, aryl lower alkyl, cycloalkyl, cycloalkyl lower alkyl or Ar—N(R3)C(O)R4;

Ar is aryl;
each R3 and R4 are independently hydrogen or lower alkyl;
X is a second drug, which drug contains an amino group or X is a nitrogen containing vitamin, an amino acid, a nucleotide, or X is N(R5)(R6)(R7) or a nitrogen containing heterocyclic ring containing 1, 2, 3 or 4 nitrogen atoms, wherein one nitrogen atom is bonded directly to the boron atom, said nitrogen atom being bonded directly to the boron atom being tetravalent;
R5, R6 and R7 are independently hydrogen, lower alkyl, cycloalkyl, cycloalkyl lower alkyl, aryl, aryl lower alkyl or heterocyclic or heterocyclic lower alkyl;
wherein, aryl, heterocyclic, cycloalkyl, R1, R2, R3, R4, R5, R6, R7, R8, R9, R10 and R11 groups being independently unsubstituted or substituted with lower alkyl, halo, lower alkoxy, heterocyclic, cycloalkyl, nitro, carboxy, carbalkoxy, CONR8R9, C(O)R8, or OC(O)R8, where R8 and R9 are independently hydrogen or lower alkyl. In an embodiment, the second drug is not nicotine or ammonia. In an embodiment, X is not ammonia $NH(CH_3)_2$, $N(CH_3)_3$ or nicotine when V is OH or $O^-$.

In an embodiment, at least one of X and V is a drug. In another embodiment, V1 may or may not be present. In an embodiment, V1 is not present when neither X nor V is a drug. In another embodiment, V1 is present when neither X nor V is a drug. In a further embodiment, V1 is present when only one of X or V is a drug. In a still further embodiment, V1 is present, when both X and V are drugs.

When V and V1 are present, in one embodiment, V and V1 are the same. In another embodiment, V and V1 are different drugs.

In an embodiment, when the compound of formula I is a pharmaceutically acceptable salt, V or V1 is $O^-$. In another embodiment, a pharmaceutically acceptable salt may be formed from a nitrogen atom on the X moiety that is not bonded to the boron atom and whose lone pair electrons are not part of a pi aromatic or heteroaromatic ring system.

As used herein, in an embodiment the salts are prepared from converting the carboxylic acid group to the ionic salts that have $Na^+$, $K^+$, or other alkali or alkaline earth metal or transition metal cation or $NH_4^+$ as cation. In another embodiment, the pharmaceutically acceptable salts are anions that are associated with a protonated nitrogen atom of organic base that is not bonded to the boron atom.

These compounds of Formula I are used for therapeutic delivery of CO to human or other mammals. The CO release rate can be varied depending on the structure of the amine group attached. Some release CO faster than others, thus, providing a range of compounds for different applications requiring a burst of CO to a low dose of CO. The molecules can be tailored to be potentially nontoxic since we can predict the products of decomposition.

In addition to the spontaneous release of CO under physiological condition, the CO release process could be expedited for amine carboxyboranes in the presence of reactive oxygen species (ROS). Further, the compounds of Formula I can be preserved in the normal cells and release low amounts of CO, but will break down faster and produce more CO in the diseased cells or cancer cells that naturally produce high amount of ROS, therefore giving a better cytoprotective effect.

Decomposition studies show not only the release of CO but also the release of the amine group upon breakdown of the compound. Thus, the compounds described herein of Formula I are used for protecting drugs or nitrogen containing vitamins or amino acids or proteins or nucleotides, bonded thereto as well as for increasing solubility, and targeting a diseased site. Since cancer cells or diseased cells produce high amount of ROS, in an embodiment, they are the perfect sites for the compound to decompose and release the drug of choice.

The compounds of Formula I are also used as protection for a non-toxic molecule, such as a drug, as described herein or a nitrogen containing vitamin, amino acid, protein, nucleotide and the like and delivery system for such molecule containing at least one amine group that can be attached to the boron atom. In an embodiment, the amine of X is a drug which is bonded to the boron atom, as described hereinbelow. In another embodiment, the drug contains a hydroxyl group, the oxygen atom of which is attached to the acyl group of the compound of Formula I. In still another embodiment, the drug contains an amino group which is attached to the acyl group of the compounds of Formula I. In still another embodiment, a drug contains an amino group which is bonded to the boron atom of the compound of Formula I. Thus, another aspect of the present disclosure is the use of the compound of Formula I as a carrier for drugs for delivery to the area of treatment. In this embodiment, V and/or V1 is esterified to a drug having a hydroxyl group or V and/or V1 forms a carboxamide bond with the acyl group of the compound of Formula I and/or X is a drug with an amino group and the amino group is bonded to the boron group of the compound of Formula I.

The inventors found that amine carboxyboranes quickly release amine group (drug molecule) in the presence of reactive oxygen species (ROS) which are prevalent in diseased cells. This property makes amine carboxyboranes a drug delivery system which can selectively release drugs at diseased sites.

The compounds of Formula I depicted above, including the esters represent a new class of CORMs that are potentially nontoxic, in contrast to many of the competing carbon monoxide (CO) delivery products and processes. Amine carboxyboranes also provide for easier synthesis and handling compared to most of the CORMs, many of which are air and water sensitive. Further, amine carboxyboranes are highly soluble in water and can provide a highly controllable release rate for CO in physiological condition and temperature without the help of inducers such as light or other chemicals.

The compounds of Formula I are useful for inhibiting the production of pro-inflammatory factors such as tumor necrosis factor α (TNF-α) and increasing the production of anti-inflammatory cytokines. This aspect of the invention relates CORCBs for treating inflammatory diseases such as sepsis, cystic fibrosis, pulmonary hypertension, arthritis, Parkinson's disease, Alzheimer's disease, and others. Moreover, they are anti-oxidants, and protect the cells from apoptosis. Therefore, the present disclosure relates to delaying or alleviating the oxidative stress which occur in cancer and organ transplantation.

BRIEF DESCRIPTION OF THE DRAWINGS

The objects, features and advantages will become apparent to one ordinary skill in the art, in view of the following detailed description taken in combination with the attached drawings, in which FIG. 1 illustrates various NMR spectra of the decompositions of exemplary CORCBs. (A) Auto-decomposition of CORCB-1, as evident by $^1H$ NMR; (B) Overlaid $^{11}B$ NMR spectra showing progression of decomposition; (C) Overlaid $^{13}C$ NMR over a period of time.

FIG. 2 graphically depicts the CO releasing property of CORCB-1 tested by traditional Mb assay. Upon incubation of deoxymyoglobin with CORCB-1 at 37° C., UV-visible spectra were collected at different time points. Deoxymyoglobin gradually turns to carboxymyoglobin in a sealed cuvette.

FIG. 3 graphically depicts the auto-decomposition of CORCB acid forms monitored by $^1$H NMR. CORCBs were dissolved in $D_2O$ and incubated at 37° C. NMR spectra were taken at specified times to track the decomposition rates.

FIG. 4 graphically depicts the auto-decomposition of CORCB salts monitored by $^1$H NMR. (A) CORCB sodium salts and (B) CORCB ammonium salts. All CORCB salts are soluble in $D_2O$ solvents. After incubation at 37° C., $^1$H NMR spectra were taken at specified times to track the decomposition rates. Sodium salts of CORCB-3, 4, and 5 had insignificant amounts of decomposition, therefore data not shown.

FIG. 5 graphically depicts the percent CO released by CORCB acid forms measured with CO meter. CORCBs were dissolved in water and incubated at 37° C. for 24 hours. The head space air that contained CO gas is analyzed by a CO meter and the ppm readings converted to the micromole amount for percent calculation.

FIG. 6 graphically depicts the percent CO released by sodium salts of CORCBs measured with CO meter. CORCB sodium salts were dissolved in water and incubated at 37° C. for 24 hours. The head space air that contained CO gas is analyzed by a CO meter and the ppm readings converted to the micromole amount for percent calculation.

FIG. 7 graphically depicts the percent decomposition of CORCBs in the presence of ROS monitored by $^1$H NMR. CORCBs were dissolved in water and 1.5 times equivalents of hydrogen peroxide was added before incubation in 37° C. $^1$H NMR spectra were taken at specified times to track the decomposition rates.

FIG. 8 graphically compares the percent decomposition of CORCBs in the presence of ROS monitored by $^1$H NMR and CO meter. CORCBS were dissolved in water and 1.5 equivalents of hydrogen peroxide were added before incubation at 37° C. for 24 hours. Measurements were taken and percent calculated. The CO meter readings represent the amount of CO released and $^1$H NMR corresponds to the amine group or drug molecule releasing property.

FIG. 9 graphically depicts CO measurements using CO meter from COCRBs in the presence of 1.5 and 3 equivalents of ROS. CORCBs were incubated with respective amounts of hydrogen peroxide for 12 hours at 37° C. and the CO concentration was measured by the CO meter.

FIG. 10 graphically depicts the percent CO generated by CORCB-1 in different pHs monitored by the CO meter. CORCB was dissolved in water with adjusted pH before incubation in 37° C. After 12 hours, CO gas in the head space was analyzed using a CO meter.

FIG. 11 graphically depicts the anti-inflammatory and cell toxicity effect of CORCB-1 tested on mouse macrophages. LPS induced TNF-alpha production was tested first and cell viability assay was performed on the same cells. Untreated cells sample was set at 100% for calculating % viability and sample treated with only LPS was normalized to 100% for calculating TNF-α percentage.

FIG. 12 graphically depicts the cell toxicity of CORCB-1 tested on mouse macrophages. Untreated sample was set to 100% for normalization. Different concentrations of CORCB were incubated with the cells for 24 hours and Cell Titer Blue reagent was added to assess the viability.

FIG. 13 graphically depicts anti-inflammatory and cell toxicity effect of CORCB-3 tested on mouse macrophages. LPS induced TNF-alpha production was tested first and cell viability assay was performed on the same cells. The data was normalized to make LPS only cells 100%.

FIG. 14 graphically depicts cell toxicity of CORCB-3 tested on mouse macrophages. Untreated sample was set to 100% Data was normalized by cells only as 100%. Different concentrations of CORCB were incubated with the cells for 24 hours and Cell Titer Blue reagent was added to assess the viability.

FIG. 15 graphically depicts the anti-inflammatory and cell toxicity effect of CORCB-1 in the presence of hydrogen peroxide tested on mouse macrophages. LPS-induced TNF-alpha production was tested first and cell viability assay was performed on the same cells. Untreated cells sample was set at 100% for calculating % viability and sample treated with only LPS was normalized to 100% for calculating TNF-α percentage.

FIG. 16 depicts graphically depicts the anti-inflammatory and cell toxicity effect of CORCB-3 in the presence of hydrogen peroxide tested on mouse macrophages. LPS-induced TNF-alpha production was tested first and cell viability assay was performed on the same cells. Untreated cells sample was set at 100% for calculating % viability, and sample treated with only LPS was normalized to 100% for calculating TNF-α percentage.

FIG. 17 graphically depicts cell growth enhancement of CORCB-1 tested on tumor cells (Hs 895.T) and normal cells (Hs 895.Sk). Data was normalized by setting untreated cells (cells only) as 100%. Different concentrations of CORCB-1 was incubated with the cells for 48 hours and Cell Titer Blue reagent was added to assess the viability.

FIG. 18 graphically depicts the effect of CORCB-6 on tumor cells (Hs 895.T) and normal cells (Hs 895.Sk). Data was normalized by setting untreated cells (cells only) as 100%. Different concentrations of CORCB-1 was incubated with the cells for 48 hours and Cell Titer Blue reagent was added to assess the viability.

FIG. 19 graphically depicts the anti-tumor activity of CORCB-1 in the presence of ROS. Fibroblast tumor cells (Hs 895.T) and normal cells (Hs 895.Sk) were treated with CORCB-1 (1 mM) in combination with $H_2O_2$ (0.2 mM). Cell viability was tested on 2, 4, and 6 days using Cell Titer Blue reagent. Data was normalized by setting untreated cells as 100%.

FIG. 20 graphically depicts cell viability by CORCB-1 in the presence of toxic drugs such as imatinib used in chemotherapy. As controls, skin fibroblast cells (Hs 895.Sk) were treated with 20 and 40 μM concentrations of imatinib. Into two other samples containing 20 and 40 μM imatinib, CORCB-1 (3 mM) was added. Cell viability was tested on 2, 4 and 6 days using Cell Titer Blue reagent. Data was normalized by setting untreated cells as 100%.

DETAILED DESCRIPTION OF THE INVENTION

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

As described hereinabove, an aspect of the present invention is directed to compounds of Formula I. As defined, the boron atom is bonded to 4 different substituents, hydrogen twice, an acyl group C(O) and X, and thus has a negative charge, which is not shown in formula I. On the other hand, the nitrogen atom bonded to the boron atom has four bonds attached thereto; the nitrogen atom is bonded to the boron atom, which accounts for one of its bonds. However, the nitrogen atom may be bonded to three other substituents or the nitrogen atom is double bonded to another atom, such as a carbon atom, and is bonded to one other substituent. Regardless of the structural configuration, this nitrogen atom is positively charged, which is also not shown in Formula I.

As used herein, the term "lower alkyl", when used alone or in combination, refers to an alkyl group which contains one to six carbon atoms. The alkyl group can be straight-chained or branched. Examples include methyl, ethyl, N-propyl, i-propyl, n-butyl, i-butyl, sec-butyl, or t-butyl, n-pentyl, i-pentyl, neopentyl or n-hexyl, and the like.

"Cycloalkyl" as used herein, includes saturated and partially unsaturated cyclic, hydrocarbon groups having 3 to 15 ring carbons atoms, up to a total of 20 carbon atoms; however, in an embodiment, it contains 5, 6, 7, 8, 9, 10, 11, 12, 13, 14 or 15 ring carbon atoms. It contains one or more rings fused to one another, wherein the ring atoms are carbon atoms. It may be monocyclic, bicyclic, tricyclic, tetracyclic or pentacyclic. In addition, it includes an alicyclic ring structure fused to one or more aromatic rings, and the like. Examples of cycloalkyl include cyclopropyl, cyclobutyl, cyclopentyl, cyclohexyl, decalinyl, norbornyl, indanyl, adamantyl, tetralinyl, indenyl, and the like.

Then term "aryl" refers to aromatic moiety ring containing only ring carbon atoms. It contains 4n+2 ring carbon atoms, wherein n is 1, 2 or 3. Thus, it may contain 6, 10 or 14 ring atoms. Examples include phenyl, α-naphthyl, β-naphthyl, anthracenyl, phenanthracenyl and the like.

The term "alkoxy" refers to an —O-alkyl radical, where alkyl is as defined herein.

As used herein, the term "halo" or "halogen" refers to any radical of fluorine, chlorine, bromine or iodine.

The term "aryl lower alkyl" refers to a moiety in which a lower alkyl hydrogen atom is replaced by an aryl group; the term cycloalkyl lower alkyl refers to a moiety in which a lower alkyl hydrogen atom is replaced by a cycloalkyl group; and the term heterocyclic lower alkyl group refers to a moiety in which a lower alkyl hydrogen atom is replaced by a heterocyclic group.

As used herein, the term "heterocyclic" refers to a fully saturated or partially unsaturated or completely unsaturated cyclic groups, for example, 3 to 7 membered monocyclic, 7 to 12 membered bicyclic, or 10 to 15 membered tricyclic ring systems, which have at least one ring heteroatom in at least one ring, wherein 0, 1, 2 or 3 atoms of each ring may be substituted by a substituent. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. However, as defined, if X is a heterocyclic moiety, it must contain at least one ring heteroatom and the nitrogen atom in the ring must be bonded to the boron atom. The heterocyclic ring that is bonded to the boron atom may contain up more than one ring heteroatom, including more than one nitrogen ring atom, such as 2, 3, or 4 nitrogen ring atoms. The term heterocyclic includes a ring system containing two or more saturated or partially saturated rings fused together containing at least one ring heteroatom fused to a cycloalkyl aromatic or another heterocyclic ring. Moreover, as used herein, the term heterocyclic includes heteroaryl, which refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system, wherein 0, 1, 2, 3, or 4 atoms of each ring may be substituted by a substituent. Examples of heterocyclics include tetrahydrofuran, furan, piperidine, piperazine, pyrrole, furan, thiophene, imidazole, oxazole, thiazole, pyrazole, pyridine, pyramiding, quinoline, quinazoline, pyrazinyl isoquinoline, purine and carbazole, benzooxazole, tetrazole, thiophene, triazine, dioxolane, imidazoline, imidazolidine, isothiazolidine, isoxazolidine, morpholine, 2-oxopiperazine, oxazolidine, pyrrolidine, pyrazolidine, thiazolidine, tetrahydrofuryl, trithianyl, tetrahydropyran, memantine, amantadine, hexamethylenetetramine (methenamine) and the like. Unless stated otherwise specifically in the specification, a heterocyclyl group may be optionally substituted with the substituents described hereinabove.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention.

As used herein, the term "drug" refer to a compound which has therapeutic properties when administered to an animal, such as a mammal, e.g., a human.

As used herein the amino acid is one of the 20 essential amino acids. Examples include glycine, alanine, leucine, isoleucine, valine, phenylalanine, proline, serine, threonine, aspartic acid, glutamic acid, asparagine, glutamine, histidine, tyrosine, methionine, cysteine, tryptophan, lysine and histidine, and the like.

As used herein a nucleotide is one of the bases of DNA or RNA and includes adenine, guanine, cytosine, thymine and uracil. In an embodiment, one of Y1 and Y2 is hydrogen. In another embodiment, both of Y1 and Y2 are hydrogen.

In an embodiment, X is aminocycloalkyl, wherein the cycloalkyl contain 1, 2, 3, or 4 rings fused together; a heterocyclic ring, containing 1, 2, 3 or 4 rings fused together which is completely saturated containing 1, 2, 3 or 4 ring nitrogen atoms or monocyclic heteroaromatic ring containing 1 or 2 ring nitrogen atoms. In another embodiment, X is cycloalkyl containing 1, 2 or 3 rings fused together, heterocyclic ring, which is completely saturated containing 1, 2 or 3 rings fused together and 1, 2, 3 or 4 ring nitrogen atoms or monocyclic heteroaromatic ring containing 1 or 2 ring nitrogen atoms. An embodiment of the present disclosure includes compounds where X is a saturated cycloalkylamine containing 1, 2, 3 rings, a 3 or 4 ring N-heterocyclic, where the heterocycle contains 1, 2, 3, or 4 ring nitrogen atoms. Examples include memantinyl, amantadinyl, hexamethylenetetramine, and the like.

In an embodiment, V is O⁻, OH or lower alkoxy or acetaminophen.

In another embodiment, V is O⁻, OH or lower alkoxy or acetaminophen and X is a saturated cycloalkylamine containing 1, 2, 3 rings, or N-hetrocyclic, where the heterocycle contains 3 rings, is completely saturated and has 1, 2, 3, or 4 ring nitrogen atoms.

In an embodiment, either X or V or both is a drug. As indicated hereinabove, V1 may also be a drug. When the drug is bonded to the acyl carbon, it has an amino or alcohol functionality thereon and forms an ester or amide bond. As such, the drug is less the hydroxyl hydrogen or is less an amino hydrogen atom. On the other hand, when X is a drug, the lone pair of electrons on the nitrogen atom of X bonds to the boron atom; thus X does not lose a hydrogen atom thereon, but is now has four bonds, as explained hereinabove.

In an embodiment, when X, which is an amine, is a drug containing an amino group, the drug is Hexamethylenetetramine, Memantine, Amantadine, Aripiprazole, Rosuvastatin, Pregabalin, Scopolamine, Sitagliptin, Glatiramer acetate, Abacavir, Abiraterone, Amlodipine, Amphetamine, Anastrozole, Atazanavir, Atomoxetine, Azacitidine, Bendamustine, Bortezomib, Buprenorphine, Celecoxib, Cinacalcet, Ciprofloxacin, Clopidogrel, Dabigatran, Dacarbazine, Darunavir, Dasatinib, Desvenlafaxine, Dexlansoprazole, Dexmethylphenidate, Dipyridamole, Duloxetine, Emtricitabine, Epinephrine, Erlotinib, Escitalopram, Esomeprazole, Eszopiclone, Fentanyl, Fingolimod, Formoterol, Guanfacine, Hydrocodone, Imatinib, Imiquimod, Lamivudine, Lenalidomide, Levothyroxine, Lidocaine, Linezolid, Lisdexamfetamine, Mesalazine, Metformin, Methylphenidate, Metoprolol, Minocycline, Naloxone, Nebivolol, Niacin, Nilotinib, Octreotide Acetate, Olanzapine, Olmesartan, Oseltamivir, Oxycodone, Oxymorphone, Paliperidone, Palonosetron, Pemetrexed, Pioglitazone, Piperacillin, Prasugrel, Quetiapine, Rabeprazole, Raloxifene, Raltegravir, Ranolazine, Regadenoson, Rifaximin, Rilpivirine, Risedronic Acid, Risperidone, Ritonavir, Rivastigmine, Rizatriptan, Salbutamol, Salmeterol, Saxagliptin, Sevelamer, Sildenafil, Solifenacin, Sunitinib, Tazobactam, Telaprevir, Temozolomide, Tenofovir, ThioTEPA, Tolterodine, Valganciclovir, Valsartan, Varenicline, Vismodegib, Ziprasidone, Zoledronic Acid or a pharmaceutically acceptable salt of any one of these drugs. In still further embodiment, X is memantinyl, amantadinyl, or hexamethylenetetramine.

In another embodiment, when V or V1 is a drug containing a hydroxy group less a hydrogen on the hydroxy group, the drug is Acetaminophen, Rosuvastatin, Scopolamine, Glatiramer acetate, Abacavir, Abiraterone, Atorvastatin, Azacitidine, Beclomethasone Dipropionate, Bimatoprost, Budesonide, Buprenorphine, Darunavir, Dasatinib, Desvenlafaxine, Dipyridamole, Emtricitabine, Enoxaparin, Epinephrine, Ethinyl Estradiol, Etonogestrel, Everolimus, Ezetimibe, Fingolimod, Formoterol, Lamivudine, Levothyroxine, Mesalazine, Metoprolol, Minocycline, Naloxone, Nebivolol, Norgestimate, Octreotide Acetate, Olmesartan, Oxycodone, Oxymorphone, Paliperidone, Quetiapine, Raloxifene, Ranolazine, Regadenoson, Rifaximin, Salbutamol, Salmeterol, Saxagliptin, Sevelamer, Solifenacin, Tacrolimus, Testosterone, Tolterodine, Travoprost or a pharmaceutically acceptable salt of any one of these compounds. In an embodiment, when V or V1 is a drug containing an amino group less a hydrogen on the amino group, the drug is Benzocaine, Pregabalin, Sitagliptin, Glatiramer acetate, Abacavir, Amlodipine, Amphetamine, Atomoxetine, Azacitidine, Cinacalcet, Darunavir, Dasatinib, Emtricitabine, Epinephrine, Erlotinib, Fingolimod, Formoterol, Guanfacine, Imiquimod, Lamivudine, Lenalidomide, Levothyroxine, Lisdexamfetamine, Mesalazine, Metformin, Methylphenidate, Metoprolol, Nebivolol, Octreotide Acetate, Oseltamivir, Pemetrexed, Regadenoson, Rifaximin, Salbutamol, Salmeterol, Saxagliptin, Sevelamer, Valganciclovir, Varenicline.

An embodiment of a hydroxyl containing drug is acetaminophen and the like.

An embodiment of the compound of formula I is a compound wherein Y1 and Y2 are both hydrogen, X is NR1R2 or is drug containing an amino group, such as the amino drugs listed hereinabove for X and V is O⁻, OH, OR10 or NHR10 or NR10R12, or a drug containing an hydroxy group or a drug containing an amino group, such as one of the drugs identified hereinabove for V. In an embodiment, the drug for X is not nicotine.

Examples of compounds of Formula I include the following:

1. Hexamethylenetetramine carboxyborane (CORCB-1)

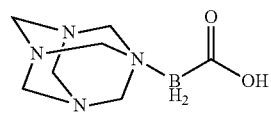

2. Pyridine carboxyborane (CORCB-2)

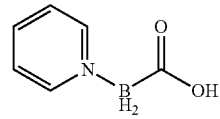

3. trimethylamine carboxyborane (CORCB-3)

4. memantine carboxyboraane (CORCB-4)

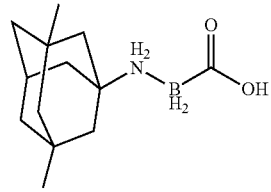

5. nicotine carboxyborane (CORCB-5)

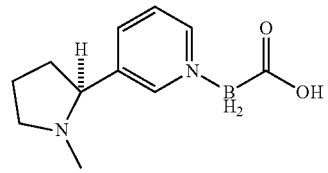

6. amantadine carboxyborane (CORCB-6)

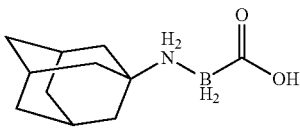

7. hexamethylenetetramine carboacetaminophenborane (CORCB-1-TY)

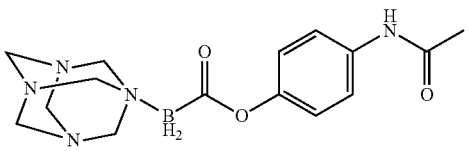

8. Trimethylamine carboethyl-4-aminobenzoateborane (CORCB-3-TY)

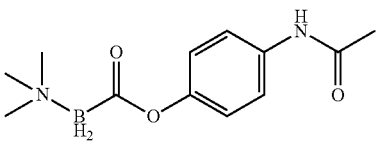

9. Trimethylamine carboacetaminophenborane (CORCB-3-BENZ)

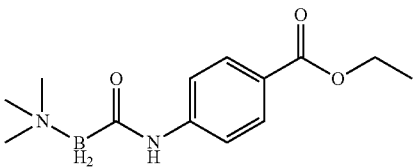

The compounds provided herein can be prepared from readily available starting materials using the following general methods and procedures, as described herein below. It will be appreciated that where typical or preferred process conditions (e.g., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography or HPLC.

The compounds of the present invention can be prepared using techniques known to one of ordinary skill in the art from readily prepared stating materials. For example, the compounds of Formula I is prepared by an amine exchange known in the art to the skilled artisan. For example, for illustrative purposes, the compound of Formula I prepared by reacting $XNH_2$ with trimethylamine carboxyborane, $N(CH_3)_3BY1Y_2COOH$ in an inert organic solvent that dissolves or suspends amines, carboxyboranes, and the products, amine carboxyboranes, such as tetrahydrofuran, dichloromethane, toluene, mixtures and the like, protected from the atmosphere in an inert gas, such as nitrogen or inert gases or using drying tubes at a temperature sufficient to effect the amine exchange, such as a temperature ranging from about 20° C. to about 90° C., and form a compound of Formula I, where V is OH. An ester thereof is formed by esterifying the compound of Formula I wherein V is OH with an alcohol ROH under esterification conditions known in the art. In an embodiment, the esterification occurs in the presence of a strong base, such as NaOH, KOH, sodium amide and the like optionally in the presence of a coupling reagent, such as N,N'-dicyclohexylcarbodiimide. The amide can be formed under amide forming conditions from the carboxy group of the compound of Formula I reacting with the amine group R1R2NH in the presence of a coupling reagent, such as DCC. In an alternative method, the carboxy group of formula I can be converted to an acid chloride using techniques known to one of ordinary skill in the art, such as by reacting same with such reagents as thionyl chloride and the like and reacting the acid chloride thus formed with the amine R1R2NH under amide forming conditions.

The compounds of the present invention form salts which are also within the scope of this invention. Reference to a compound of the present invention herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound with an amount of acid or base, such as an equivalent amount, in a medium such as one in which the salt precipitates or in an aqueous medium followed by lyophilization.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, beta-hydroxybutyrate, glycolate, maleate, tartrate, methanesulfonate, propanesulfonate, naphthalene-1-sulfonate, naphthalene-2-sulfonate, mandelate and the like salts.

The compounds which contain an acidic moiety, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (e.g., organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

The compounds which contain a basic moiety, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (e.g., those formed with sulfuric acid), sulfonates (e.g., those mentioned herein), tartrates The compounds of Formula I can form basic salts using techniques known in the art. For example, the following are exemplary:

Base Type 1 $(M_a^{m+}(A^{a-})_m$:

M can be any metals such as $Li^+$, $Na^+$, $K^+$, $Rb^+$, $Cs^+$, $Ag^+$, $Mg^{2+}$, $Ca^{2+}$, $Sr^{2+}$, $Ba^{2+}$, $Zn^{2+}$, $Cd^{2+}$, $Al^{3+}$, $Bi^{3+}$ and the like. $A^{a-}$ is a counterion and can be $OH^-$, $HCO_3^-$, $CO_3^{2-}$ and the like, whereby a is an integer from 1 to 4 and m is an integer from 1 to 4.

Method A: The carboxyl group on CORCB (R1R2R3NBY1Y2COOH) can react with base $(M^{m+}(OH)_m)$ to yield $(R1R2R3NBY1Y2COO^-)_m M^{m+}$. Any carboxylate group on the first drug can also react with the base $(M^{m+}(OH)_m)$. For example:

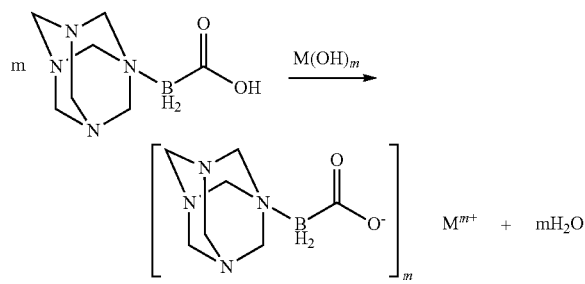

Method B: ion exchange method which is a commonly known method in the art (*Tetrahedron* (2003) 59:579-593 (Scheme 30)). For example, the following is exemplary for purposes of illustration (the equation not balanced).

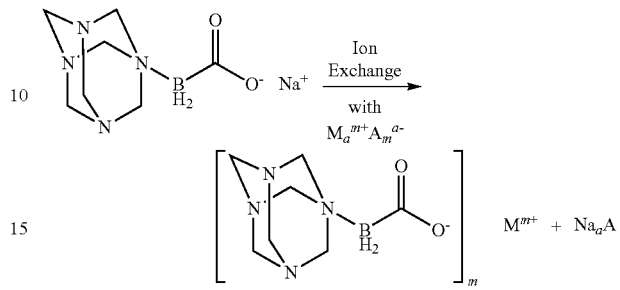

Base Type 2 (Amines)

Another method is to react the carboxylic acid with an amine Amines can be primary amines, secondary amines, tertiary amines, cyclic amines, and the like containing, for example 1-6 carbon atoms if straight chain or 5-14 ring carbon atoms if cyclic or are an aromatic amine, such as aniline. Examples include such amines as ammonia, methylamine, dimethylamine, trimethyamine, cyclohexylamine, piperidine, hexylamine and the like. The amines can be amino acids, peptides, proteins, nucleic acids, nucleotides, targeting signals, signaling molecules and the like.

Using ammonia as a an example, the amine reacts with the carboxylic acid as illustrated below

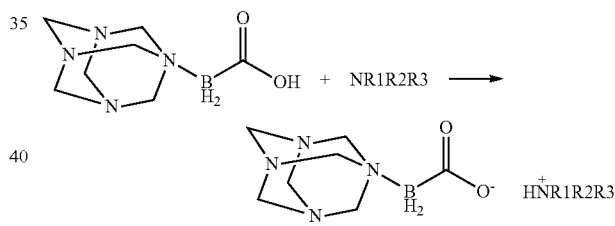

The compounds of Formula I are metabolized in vivo to release carbon monoxide. For example, in vivo under physiological conditions, CO is produced. Without wishing to be bound, it is believed that a compound of Formula I breaks down into the amine, $XNH_2$, $B(OH)_3$, and carbon monoxide. Since the compounds of Formula I generate carbon monoxide in vivo, they are useful for the treatment of vascular, inflammatory and immune disorders in a patient. In a further embodiment, the present invention provides methods and compositions for modulating inflammatory and immune processes throughout the body. The subject compounds are capable of modulating the activity of various immune system cells, inhibiting the production of pro-inflammatory cytokines and enhancing production of anti-inflammatory cytokines by cells capable of producing such cytokines, thereby being effective in the treatment of conditions associated with adverse inflammatory responses. Thus, an embodiment of the present invention relates to a method of delivering therapeutic carbon monoxide to the cells and tissues of a patient which comprises administering thereto the compound of Formula I or pharmaceutically acceptable salt thereof. In an embodiment, the second drug is not nicotine or ammonia and further provided that X is not ammonia and further provided that X cannot be NH(CH₃)₂, N(CH₃)₃ or nicotine when V is OH or An embodiment of the present invention is a method of delivering therapeutic carbon monoxide to the cells and tissues of a patient which comprises administering thereto a compound of the formula

or pharmaceutically acceptable salts,
where
each Y1 and Y2 may be the same or is different and is independently H, alkyl, halo, CN or C(O)V1;
V is O⁻, OR1 or NR1R2 or is a first drug, which drug has an amino function or an alcohol moiety thereon in which a hydrogen atom of the alcohol or amine is not present;
V1 is O⁻, OR10 or NR10R12 or is a third drug, which drug has an amino function or an alcohol moiety thereon in which a hydrogen atom of the alcohol or amine is not present;
R1, R2, R10 and R12 are independently hydrogen, lower alkyl, aryl, aryl lower alkyl, cycloalkyl, cycloalkyl lower alkyl or Ar—N(R3)C(O)R4 or is a first drug, which drug has an amino function or an alcohol moiety thereon in which a hydrogen atom of the alcohol or amine is not present;
Ar is aryl;
each R3 and R4 are independently hydrogen or lower alkyl;
X is a second drug, which drug contains an amino group or X is a nitrogen containing vitamin, an amino acid, a nucleotide, or X is N(R5)(R6)(R7) or a nitrogen containing heterocyclic ring containing 1, 2, 3 or 4 nitrogen atoms, wherein one nitrogen atom is bonded directly to the boron atom, said nitrogen atom being bonded directly to the boron atom being tetravalent;
R5, R6 and R7 are independently hydrogen, lower alkyl, cycloalkyl, cycloalkyl lower alkyl, aryl, aryl lower alkyl or heterocyclic or heterocyclic lower alkyl;
wherein, aryl, heterocyclic, cycloalkyl, R1, R2, R3, R4, R5, R6, R7, R8, R9, R10 and R11 groups being independently unsubstituted or substituted with lower alkyl, halo, lower alkoxy, heterocyclic, cycloalkyl, nitro, carboxy, carbalkoxy, CONR8R9, C(O)R8, or OC(O)R8, where R8 and R9 are independently hydrogen or lower alkyl.

R8 and R9 being independently hydrogen or lower alkyl. In this embodiment, X can be nicotine or ammonia, NH(CH₃)₂, or N(CH₃)₃ when V is OH or O⁻.

The compounds of the present invention are useful for extending the survival of an organ transplant in a subject wherein those methods comprise administering to said recipient a compound of Formula I. The compound of Formula I modulate the immune response against the transplanted organ, whereby the survival time of the organ transplant in the recipient is extended. Administration of the compound of Formula I may be ex vivo of an organ to be transplanted or in vivo by any convenient means, including parental, systemic or localized administration, in sufficient amount to substantially inhibit lymphocyte activation and the inflammatory process through modulation of anti- and pro-inflammatory cytokine production.

In the vasculature, the subject compounds are capable of regulating vascular tone, inhibiting VSMC (vascular smooth muscle cells) proliferation and protecting against oxidative stress and hypoxia, which have profound effects on vascular tone, endothelial permeability and coagulating function. The compounds of Formula I find use in treating vascular proliferative diseases and other disorders associated with HO-1 induction in response to oxidative stress. Thus, in an embodiment, the compounds of Formula I find use for regulating vascular tone, inhibiting VSMC proliferation and protecting against oxidative stress, thereby being useful for treating various disorders such as atherogenesis, restenosis, pressure or volume overload of the heart, hypertension, subarachnoidal hemorrhage, neointima formation and development, vasoconstriction, edema in the lung, and thrombus formation in the venous circulation In one embodiment, the compounds of Formula I are useful for inhibiting neointimal formation and improving the outcome of invasive vascular procedures by administering to a patient undergoing a procedure requiring or involving arterial injury such as balloon angioplasty the compound of Formula I to the subject; the compounds of Formula I protect against neointimal development. In another embodiment, the compounds of Formula I are employed to prevent atherogenesis, either in response to a specific oxidative event in the vasculature or prophylactically in patients at higher risk, such as, e.g., those with high levels of low-density lipoproteins (LDL) thought to be involved in atherogenesis. Administration of the compounds of Formula I may be by any convenient means, including parental, systemic or localized administration, in sufficient amount to substantially inhibit VSMC proliferation and modulate the vascular response to oxidative stress.

Another embodiment provides methods and compositions for modulating inflammatory and immune processes in vitro and in vivo. The compounds of Formula I find use for inhibiting the production of inflammatory cytokines and enhancing the production of anti-inflammatory cytokines, including TNF-alpha, interferons such as interferon-gamma, interleukins such as IL-1, IL-4, IL-5, IL-6, IL-8, IL-10, IL-12, IL-13, IL-16, MIP1-alpha, chemokines, hematopoietic growth factors and the like, thereby being useful for inhibiting inflammatory responses associated with various disorders such as rheumatoid arthritis, septic shock, Crohn's disease, colitis, multiple sclerosis, granulomatous inflammation, hepatitis, allergic reactions, autoimmune diseases, ischemic/reperfusion injury, and the like, and delaying the onset of IDDM in a patient at risk for developing IDDM, both in vitro and in vivo. In a particularly preferred embodiment, the subject compounds find use in treating rheumatoid arthritis, improving the outcome of organ transplantation (e.g, kidney, liver, heart, etc.) and preventing ischemia/reperfusion injury.

The compounds of Formula I will function both in vivo and in vitro to modulate inflammation and/or the immune response in a host or sample, respectively, into which they are introduced. The modulation will generally be exemplified by an inhibition of the expression of pro-inflammatory cytokines and/or an increase in the production of anti-inflammatory cytokines. Reliable and sensitive assays for determining the expression levels of such cytokines are well known and commercially available from such sources as BioSource International, Inc. in Camarillo, Calif.

When a drug is attached to the compound of Formula I, the compounds of the present invention may be used as a prodrug for delivery of drugs at sites where reactive oxygen species are prevalent. The release of carbon monoxide from compounds of Formula I is increased in the presence of reactive oxygen species (ROS). Thus compounds of Formula I can be preserved in the normal cells and release low amounts of CO, but will break down faster and produce more CO in the diseased cells or cancer cells that naturally produce high amount of ROS therefore giving a better cytoprotective effect.

Decomposition studies show not only the release of CO but also the release of amine group upon breakdown of the compound. This process is useful for protecting the drugs as well as for increasing solubility, and targeting a diseased site. Since most diseased cells produce high amount of ROS, they are the perfect sites for the compound to decompose and release the drug of choice.

Thus, compounds of Formula I can be used as a drug protection and delivery system for any drug containing amine group that can be attached to the boron atom of the compounds of Formula I. This new discovery shows that compounds of Formula I quickly release amine group (drug molecule) in the presence of reactive oxygen species (ROS) which are prevalent in diseased cells. This property makes the compounds of Formula I a drug delivery system which can selectively release drugs at diseased sites. Once released, these drugs have the utility attributed. For example, CORCB-1 has the drug molecule hexamethylenetetramine (HMTA), which is a bactericidal agent used for urinary tract infections, bonded to the boron atom; CORCB-4 has the drug molecule memantine, which is used to treat dementia associated with Alzheimer's disease, bonded to the boron atom; CORCB-6 has the drug molecule amantadine, which is used to treat Parkinson's disease, bonded to the boron atom; CORCB-1-TY has the drug molecules HMTA, which is a bactericidal agent, and acetaminophen, which is a pain reliever, attached; CORCB-3-TY has the drug molecule acetaminophen, which is a pain reliever, bonded to the boron atom; and CORCB-3-BENZ has the drug molecule benzocaine, which is a local anesthetic, bonded to the boron atom. Once released, these drug molecules have the utility ascribed to them.

In accordance therewith, these drug delivery compositions are prepared by conducting an amine exchange of a trimethylamine carboxyborane or any other trialkylamine carboxyborane with a drug having an amine functionality thereon under the conditions described hereinabove, using one or more protecting groups, where necessary to protect moieties thereon which are reactive under the conditions.

Alternatively, or in addition, a drug which is an alcohol or has a free amine, i.e. that has a free OH group or amine, respectively thereon, can be esterified to the carboxy end of the compound of a carboxyborane molecule of Formula I under esterifying conditions or can form an amide at the carboxy end of the compound of Formula I under amide forming conditions, respectively and the drug can be released at the site where reactive oxygen species are prevalent.

Reactive oxygen species (ROS) are produced as part of cellular metabolic process with the main source being oxidative phosphorylation. However, the level of ROS is strictly under control by various antioxidant systems present in the cells. These include, enzymatic systems such as superoxide dismutases (SODs), thioredoxins and glutathione systems plus cellular antioxidants such as flavinoids and vitamins Examples of ROS include superoxide ($O_2.^-$, hydroxyl radical (.OH), organic radicals (R13.), where R13 is a hydrocarbyl group (an organic radical comprised of carbon and hydrogen which may be straight chained or branched cycle or aromatic, and which has from 1 to 15 carbon atoms), peroxyl radicals (R13OO.), alkoxyl radicals (R13O.), thiyl radicals (R10S.), sulfonyl radicals (R13OS.), and thiyl peroxyl radicals (R13SOO.). In addition, ROS may be non-radical and include hydrogen peroxide ($H_2O_2$), singlet oxygen ($^1O_2$), ozone ($O_3$), organic hydroperoxides (R13OOH), and reactive lipid- or carbohydrate derived carbonyl compounds.

The imbalance between ROS and antioxidants results in various deteriorating conditions. As growing evidences show that ROS are either the cause or the effect of most of the diseases, the compounds of Formula I exploit this fact and target specific sites with high ROS level. Thus, the compounds of Formula I can release the drugs selectively at diseased sites. Potential usage includes but not limited to the following. Once released, the drugs have the utility associated with the drug:

1. Neurodegenerative diseases such as Parkinson's, Alzheimer's and amyotrohic lateral sclerosis (ALS) have long been known to be associated with oxidative stress caused by ROS. Protein oxidation and lipid peroxidations have been reported in the patients with these diseases, indicating that ROS is prevalent in these diseases. The drugs used to treat these diseases will be much better targeted and released at the site where ROS is concentrated when synthesized in formula I.

2. Cancers and elevated level of ROS are almost always found together. Therefore, it has been postulated that ROS may play a role in initiation and progression of carcinogenesis. New models suggest that cancer cells increase the production of ROS to activate localized pro-tumorigenic signaling. Therefore, the compounds of the present invention have therapeutic utility in suppression of ROS or exacerbation of ROS by disabling antioxidants to induce cell death. In addition, advantage is taken of this high ROS state and a much larger dose of chemotherapy drugs that can be targeted to selectively kill cancer cells without causing much side effects to other tissues. Masking chemotherapy drugs with compounds of Formula I will release the drugs only in cancer cells having high ROS and deliver the effect.

3. Recent studies suggest that human inflammatory diseases (HIDs) such as rheumatoid arthritis, type 2 diabetes, and atherosclerosis may have stemmed from excessive generation of ROS causing uncontrolled inflammatory response. These diseases can be better targeted to the affected sites and the thus can be treated when the medicines are released at the areas with high ROS in which the drug is bonded to the carboxyboranes prepared as described herein using compounds of Formula I.

4. Viral and bacterial infections are combated by the body defense mechanism that involves recruitment of macrophages and phagocytes which exert microbicidal effect by producing excessive oxidative stress. Hepatitis B (HBV) and hepatitis C (HCV) virus infections are found to be associated with increased production of ROS in the liver. HIV-positive individuals exhibit chronic oxidative stress with decreased concentrations of cellular antioxidant reductants such as thiols, cysteine, and glutathione in combination with elevated levels of oxidants such as hydroperoxides and malondialdehyde. The main pathogen elimination process by the body starts with NADPH-oxidase (NOX-2) promoting oxidative mechanism causing respiratory burst in the phagosome. Since ROS is abundant in infected sites, administering the compound of Formula I, the drug moiety attached thereto, when released by the reactive ROS, can selectively deliver anti-viral and anti-bacterial drugs therefore effectively destroying the pathogens.

The compounds of Formula I may be formulated in a variety of ways, depending upon the nature and purpose of administration, the specific inflammatory disease being treated, the particular generating compound, the number of administrations, the inclusion or use of other drugs, and the like, and such may be determined empirically by those skilled in the art. The formulation will generally be in a physiologically acceptable form, and may include various carriers or solvents such as water, deionized water, phosphate buffered saline, aqueous ethanol, glucose, propylene glycol, vegetable oils, olive oil or the like. In some instances, the subject carbon monoxide generating compounds may be formulated in a slow release formulation, where the subject compounds may be encapsulated in a wide variety of carriers, may be administered as capsules, or as a prodrug. The formulations may also include, stabilizers, buffers, or the like.

The compounds of Formula I or their pharmaceutically acceptable salt thereof is associated with a pharmaceutically acceptable carrier using techniques known in the art. The term "pharmaceutically acceptable carrier" refers to a diluent, adjuvant, excipient or carrier with which a compound of the invention is administered.

The compounds of Formula I in association with a pharmaceutical carrier are administered to a subject or patient. A "subject" or "patient" to which administration is contemplated includes, but is not limited to, humans (i.e., a male or female of any age group, e.g., a pediatric subject (e.g., infant, child, adolescent) or adult subject (e.g., young adult, middle-aged adult or senior adult). In an alternative embodiment, the subject can be a non-human animal, e.g., a mammal such as primates (e.g., cynomolgus monkeys, rhesus monkeys), cattle, pig, horse, sheep, goat, rodent, cat, and or dog. Unless otherwise indicated, the term subject in a claim refers to a human.

The compounds of Formula I can be provided, if desired, as a pharmaceutically acceptable salt or a pharmaceutically acceptable composition thereof to treat a disorder or disease described herein. The terms "ameliorate" and "treat" are used interchangeably and both mean decrease, suppress, attenuate, diminish, arrest, or stabilize the development or progression of a disease (e.g., a disease or disorder delineated herein). By "disease" is meant any condition or disorder that damages or interferes with the normal function of a cell, tissue, or organ.

In one embodiment, a compound of Formula I or its pharmaceutically acceptable salt can be administered in a pharmaceutical composition suitable for oral delivery to the patient, typically a human. Alternatively, a compound of Formula I or its pharmaceutically acceptable salt can be delivered in a carrier suitable for topical, intravenous, parenteral, subcutaneous or other desired delivery route, including any method of controlled delivery, for example, using degradable polymers, or with nano or microparticles, liposomes, layered tablets or other structural frameworks which slow delivery.

The compound of Formula I can be in the form of a salt. It can be administered as a pharmaceutically acceptable salt, for example, a pharmaceutically acceptable acid addition salt, including a hydrochloride, hydroiodide, hydrobromide, nitrate, sulfate, bisulfate, phosphate, acetate, lactate, citrate, tartrate, succinate, maleate, fumarate, benzoate, para-toluenesulfonate and the like.

The compounds of Formula I or its pharmaceutically acceptable salt provided herein are administered for medical therapy in a therapeutically effective amount. The amount of the compound of Formula I or its pharmaceutically acceptable salt administered will typically be determined by a physician, in the light of the relevant circumstances, including the condition to be treated, the chosen route of administration, the compound or salt administered, the age, weight, and response of the individual patient, the severity of the patient's symptoms, and the like. Applying these factors, in an embodiment, the dose is generally in the range of about 0.001 mg/kg to about 2000 mg/kg In accordance with the present invention, the compounds of the present invention are administered as pharmaceutical compositions. The term "pharmaceutical composition" relates to a composition for administration to a patient, preferably a human patient. The pharmaceutical composition of the invention comprises the compounds recited above. The pharmaceutical composition of the present invention may, optionally and additionally, comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, organic solvents including DMSO etc. Compositions comprising such carriers can be formulated by well known conventional methods The pharmaceutical compositions provided herein can be administered by a variety of routes including oral, topical, nasal, systemic, parenteral, transdermal, subcutaneous, intravenous, intra-arterial, intraperitoneal, intramuscular with a pharmaceutical carrier suitable for such administration. In one embodiment, the compound of one of the Formulas or its pharmaceutically acceptable salt is administered in a controlled release formulation.

The formulation includes the compound of Formula I, as either a weight ratio or as a weight amount. It is to be understood, unless indicated to the contrary, that the weight amount and weight ratios are based upon the molecular weight of the compound of Formula I, even if the formulation contains the salt form thereof.

The pharmaceutical composition is also suitably administered by sustained release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58 481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., J. Pharm. Sci. 12:1859-1861 (1984)) or poly-D-(−)-3-hydroxybutyric acid (EP 133 988). Sustained release pharmaceutical composition also include liposomally entrapped compound. Liposomes containing the pharmaceutical composition are prepared by methods known per se: DE 32 18 121; Epstein et al., Proc. Natl. Acad. Sci. (USA) 82:3688-3692 (1985); Hwang et al., Proc. Natl. Acad. Sci. (USA) 77:4030-4034 (1980); EP 52 322; EP 36 676; EP 88 046; EP 143 949; EP 142 641; Japanese Pat. Appl. 83-118008; U.S. Pat. Nos. 4,485,045 and 4,544,545; and EP 102324. Ordinarily, the liposomes are of the small (about 200-800 Angstroms) unilamellar type in which the lipid content is greater than about 30 mol % cholesterol, the selected proportion being adjusted for the optimal therapy.

For parenteral administration, the pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the components of the pharmaceutical composition uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient.

Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The components of the pharmaceutical composition to be used for therapeutic administration must be sterile. Sterility is readily accomplished by filtration through sterile filtration membranes (e.g., 0.2 μm membranes). Therapeutic components of the pharmaceutical composition generally are placed into a container having a sterile access port, for example, an intravenous solution bag or vial having a stopper pierceable by a hypodermic injection needle.

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

The pharmaceutical composition will be formulated and dosed in a fashion consistent with good medical practice, taking into account the clinical condition of the individual patient, the site of delivery of the pharmaceutical composition, the method of administration, the scheduling of administration, and other factors known to practitioners. The "effective amount" of the pharmaceutical composition for purposes herein is thus determined by such considerations. The skilled person knows that the effective amount of pharmaceutical compositions administered to an individual will, inter alia, depend on the nature of the compound.

As used herein the term "therapeutically effective amount" refers to an amount sufficient to elicit the desired biological response.

The compositions for oral administration can take the form of bulk liquid solutions or suspensions, or bulk powders. Typically, the compositions are presented in unit dosage forms to facilitate accurate dosing. The term "unit dosage forms" refers to physically discrete units suitable as unitary dosages for human subjects and other mammals, each unit containing a predetermined quantity of active material of the compound of Formula I or its pharmaceutically acceptable salt calculated to produce the desired therapeutic effect, in association with a suitable pharmaceutical excipient. Typical unit dosage forms include prefilled, pre-measured ampules or syringes of the liquid compositions or pills, tablets, capsules or the like in the case of solid compositions. In such compositions, the compound of Formula I or its pharmaceutically acceptable salt may be present as a minor component (as a nonlimiting example,) from about 0.1 to about 100% by weight with the remainder, if any, being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring. The compounds of Formula I are present in this form in a therapeutically effective amount. For example, the amount ranges from about 0.001 mg/kg to about to 500 mg/kg in one embodiment, and in another embodiment, from about 1 mg/kg to about 500 mg/kg and in another embodiment, from about 2 mg/kg to about 12 mg/kg.

Injectable compositions comprised of a compound of Formula I or its pharmaceutically acceptable salts are contemplated within the present disclosure. These injectable solutions use injectable carriers known within the art, such as injectable sterile saline or phosphate-buffered saline carriers and the like. The compounds of Formula I are present in this form in a therapeutically effective amount. For example, the amount ranges from about 0.001 mg/kg to about 2000 mg/kg in one embodiment, and in another embodiment, from about 0.001 mg/kg to about 500 mg/kg and in another embodiment, from about 1 mg/kg to about 60 mg/kg.

Transdermal compositions are typically formulated as a topical ointment or cream containing the compound of Formula I or its pharmaceutically acceptable salt, for example in an amount ranging from about 0.01 to about 20% by weight, in another embodiment, from about 0.1 to about 20% by weight, in still another embodiment, from about 0.1 to about 99.5% by weight. When formulated as an ointment, the compound of Formula I or its pharmaceutically acceptable salt will typically be combined with either a suitable delivery polymeric composition, or a paraffinic or a water-miscible ointment base. Alternatively, the compound of Formula I or its pharmaceutically acceptable salt may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein. The compounds of Formula I are present in this form in a therapeutically effective amount. For example, the amount ranges from about 0.01% to about 50 wt % in one embodiment, and in another embodiment, from about 0.1% to about 40 wt % and in another embodiment, from about 1% to about 50 wt %.

The compound of Formula I or its pharmaceutically acceptable salt can be administered by a transdermal device. Transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compound of Formula I or its pharmaceutically acceptable salt can also be administered in sustained release forms or from sustained release drug delivery systems. A description of representative sustained release materials can be found in *Remington's Pharmaceutical Sciences.*

The following non-limiting examples further illustrate the present invention.

Syntheses of Carbon Monoxide Releasing Carboxyboranes (CORCBs):

Example A—Synthesis of Hexamethylenetetramine Carboxyborane (CORCB-1)

Hexamethylenetetramine carboxyborane (CORCB-1) was prepared by amine exchange reaction using trimethylamine carboxyborane (CORCB-3). Trimethylamine carboxyborane (117 mg, 1.0 mol) and hexamethylenetetramine (280 mg, 2.0 mol) were dissolved in chloroform (8.0 mL), protected from the atmosphere by purging with $N_2$ gas, and maintained at 25 to 60° C. for 24 hours. The solution was purged with $N_2$ gas for 5 minutes and concentrated by vacuum distillation leaving white solid crude product (208 mg). The residue was purified by column chromatography on alumina (8 grams). The column was eluted with ethyl acetate/acetone gradient elution. CORCB-1 was collected from the second fraction as a white solid (58 mg, 29%): HRMS (pos. ion ESI) m/z: [M]$^+$ Clad for $C_7H_{15}BN_4O_2$ 198.1403; Found 198.1395; Anal. Calcd for $C_7H_{15}BN_4O_2$: C, 42.46; H, 7.63; N, 28.29. Found: C, 42.63; H, 7.65; N, 28.32; $^1$H NMR in DMSO-d6 shows δ 1.71 (m, 2H, $BH_2$), δ 4.42 (d, 3H, axial $CH_2$, J=12.2 Hz), δ 4.52 (d, 3H, equatorial $CH_2$, J=12.6 Hz), δ 4.68 (s, 6H, $CH_2$), δ 10.24 (s, 1H, $CO_2H$); $^{13}$C NMR (DMSO-d6) δ 71.05 (C-3,6,7), δ 75.80 (C-2,4,5); $^{11}$B NMR (DMSO-d6) δ −15.00 (br. s, 1B); FT-IR (solid, ATR) 1674 cm$^{-1}$ (C=O), 2379 cm$^{-1}$ ($BH_2$), 2850-3300 cm$^1$ (O—H).

Example B—Synthesis of Pyridine Carboxyborane (CORCB-2)

Pyridine carboxyborane (CORCB-2) was prepared from CORCB-3 through amine exchange reaction. Trimethylamine carboxyborane (60 mg, 0.50 mmol) was dissolved in pyridine (1.5 mL), protected from the atmosphere by purging with $N_2$ gas, and maintained at 40-70° C. for 24 hours. The solution was purged with $N_2$ gas for 5 minutes and concentrated by vacuum distillation leaving white solid crude product (70 mg). The residue was purified by recrystallization in dichloromethane and hexane to yield a white solid (40 mg, 59%): $^1$H NMR ($D_2O$) δ 2.19-3.58 (br. m, $BH_2$), δ 7.77-7.91 (m, 2H, CH), δ 8.24-8.38 (m, 2H, CH), δ 8.52-8.65 (m, 2H, CH); $^{13}$C NMR (CDCl$_3$) δ 126.44, 142.01, 148.02; $^{11}$B NMR (CDCl$_3$) δ −11.44 (t, 1B); FT-IR (solid, ATR) 1645 cm$^{-1}$ (C=O), 2396 cm$^{-1}$ ($BH_2$), 2465-3330 cm$^{-1}$ (C—H and O—H).

Example C—Synthesis of Trimethylamine Carboxyborane (CORCB-3)

Trimethylamine carboxyborane (CORCB-3) was prepared with a few modifications on the procedures from literature described in an article by Spievogel et al., (*JACS* (1980) 102:6343-6344) in which NaBH$_3$CN was reacted under reflux with trimethylammonium hydrochloride and the resulting product was first reacted with Et$_3$OBF$_4$ in methylene chloride under reflux and the product thereof was reacted with sodium hydroxide and acidified with hydrochloric acid. This literature procedure yields 61-83% of CORCB-3. A higher purity product was obtained by recrystallization in chloroform and acetone to yield white solid with 86-92% recovery: $^1$H NMR ($D_2O$) δ 1.38-2.72 (br. m, $BH_2$), δ 2.86 (s, 3H, $CH_3$); $^{13}$C NMR (CDCl$_3$) δ 51.78; $^{11}$B NMR (CDCl$_3$) δ −10.29 (t, 1B); FT-IR (solid, ATR) 1645 cm$^{-1}$ (C=O), 2382 cm$^{-1}$ ($BH_2$), 2649-3350 cm$^{-1}$ (C—H and O—H Example D—Synthesis of Memantinecarboxyborane (CORCB-4)

Memantinecarboxyborane (CORCB-4) was prepared as follows. Trimethylamine carboxyborane (CORCB-3) (117 mg, 1.0 mmol) and memantine (780 mg, 4.4 mmol) were dissolved in THF (8.0 mL), protected from the atmosphere by purging with $N_2$ gas, and maintained at 67° C. for 24 hours. The solution was concentrated by vacuum distillation leaving white solid crude product (208 mg). The residue was purified by recrystallization in dichloromethane and hexane to yield a white solid (15 mg, 6.3%): HRMS (pos. ion ESI) m/z: [M]$^+$ Calcd for $C_{13}H_{24}BNO_2$ 237.1900; Found 237.1895; $^1$H NMR (CDCl$_3$) δ 0.89 (s, 6H, $CH_3$), δ 1.08-2.64 (br. m, 15H, memantine and $BH_2$), δ 3.67-4.15 (br. m, 2H, $NH_2$), δ 8.46 (br. s, 1H, $CO_2H$); $^{13}$C NMR (CDCl$_3$) δ 29.91, δ 30.03, δ 32.78, δ 40.00, δ 42.24, δ 47.33, δ 50.22, δ 55.32; $^{11}$B NMR (CDCl$_3$) δ −21.60 (br. s, 1B); FT-IR (solid, ATR) 1624 cm$^{-1}$ (C=O), 2429 cm$^{-1}$ ($BH_2$), 2839-2947 cm$^{-1}$ (C—H), 3094-3300 cm$^{-1}$ (O—H).

Example E—Synthesis of Memantinecarboxyborane Sodium Salt (Na—CORCB-4)

Memantinecarboxyborane sodium salt (Na—CORCB-4) was prepared as follows. Memantinecarboxyborane (CORCB-4) (420 mg, 1.8 mmol) was dissolved in dichloromethane (10 mL). A mixture between sodium hydroxide (116 µL, 15.21 M) and water (25 mL) was mixed with the CORCB-4 solution and stirred for 10 minutes. Aqueous layer was separated from the mixture and the organic layer was washed with water (3×5 mL). Combine aqueous layer was dried under vacuum distillation to yield white solid (300 mg, 65%): HRMS (neg. ion ESI) m/z: Calcd for $C_{13}H_{23}BNO_2$ 236.1827; Found 236.1829; $^1$H NMR ($D_2O$) δ 0.85 (s, 6H, $CH_3$), δ1.05-2.38 (br. m, 15H, memantine and $BH_2$); $^{13}$C NMR ($D_2O$) δ 29.27, δ 29.68, δ 31.71, δ 38.83, δ 41.70, δ 46.29, δ 49.57, δ 53.77; $^{11}$B NMR ($D_2O$) δ −21.52 (br. s, 1B); FT-IR (solid, ATR) 1600 cm$^{-1}$ (C=O), 2360 cm$^{-1}$ ($BH_2$), 2740-2990 cm$^{-1}$ (C—H).

Example F—Synthesis of Nicotinecarboxyborane (CORCB-5)

Nicotine carboxyborane (CORCB-5) was prepared as follows. Trimethylamine carboxyborane (117 mg, 1.0 mmol) and nicotine (2.40 mL) were mixed, protected from the atmosphere by purging with $N_2$, and maintained at 25-67° C. for 24 hours. The solution was purged with $N_2$ gas for 5 minutes and hexane (22.5 mL) was added to the reaction mixture. The solid was separated and washed with hexane (20 mL). The solid was purified by recrystallization in dichloromethane and hexane to yield a white solid (184 mg, 84%): $^1$H NMR (D$_2$O) δ 2.08-2.33 (br. m, 3H, CH$_3$), δ 2.34-3.75 (br. m, 8H, nicotine and BH$_2$), δ3.89-4.07 (m, 1H, CH), δ 7.91-8.04 (m, 1H, CH), δ 8.42 (d, 1H, CH, J=8.1 Hz), δ 8.60-8.79 (m, 2H, 2×CH); $^{13}$C NMR (D$_2$O) δ 21.96, δ 32.47, δ 39.08, δ 56.48, δ 68.35, δ 126.62, δ 137.75, δ 141.00, δ 147.86, δ 147.92; $^{11}$B NMR (D$_2$O) δ −11.06 (br. s, 1B); FT-IR (solid, ATR) 1622 cm$^{-1}$ (C—C aromatic), 1643 cm$^{-1}$ (C=O), 2402 cm$^{-1}$ (BH$_2$), 2600-3300 cm$^{-1}$ (O—H).

Example G—Synthesis of Amantadine Carboxyborane (CORCB-6)

Amantadine carboxyborane (CORCB-6) was prepared as follows. Trimethylamine carboxyborane (CORCB-3) (2.00 g, 17.1 mmol) and amatadine (3.20 g, 21.3 mmol) were dissolved in chloroform (10.0 mL), protected from the atmosphere by using drying tube, and maintained at 50-60° C. for 24 hours. The solution was purged with N$_2$ gas for 5 minutes and concentrated by vacuum distillation leaving white solid crude product (5.10 g). The residue was purified by method A and/or method B.

Method A: The crude product was purified by recrystallization in dichloromethane and hexane to yield a white solid (980 mg, 27%): HRMS (neg. ion ESI) m/z: [M-H]$^-$ Calcd for C$_{11}$H$_{19}$BNO$_2$ 208.1509; Found 208.1513; $^1$H NMR (DMSO-d6) δ 1.30-1.88 (br. m, 12H, CH$_2$ amantadine and BH$_2$), δ 2.01 (s, 3H, CH amantadine), δ 5.13 (br. s, 2H, NH$_2$), δ 10.03 (br. s, 1H, CO$_2$H); $^{13}$C NMR (DMSO-d6) δ 28.62, δ 35.74, δ 39.79, δ 51.30; $^{11}$B NMR (DMSO-d6) δ −22.21 (br. s, 1B).

Method B: The crude product with higher percent of desired product was obtained by recrystallization in acetone and water or CORCB-3 was removed from the crude product by washing with water. The crude product was suspended in chloroform and water and pH was adjusted to higher than pH=10. Organic layer was separated out and the aqueous was wash with chloroform several times. The aqueous layer pH was adjusted to lower than pH=7. Solid product was separated by filtration to yield a white solid with 55-90% recovery.

Example H—Synthesis of Amantadine Carboxyborane Sodium Salt (Na—CORCB-6)

Amantadine carboxyborane sodium salt (Na—CORCB-6) was prepared as follows. Amantadine carboxyborane (CORCB-6) (100 mg, 0.48 mmol) was dissolved in chloroform (5 mL). Sodium hydroxide (1.94 M) was added to the CORCB-6 solution until the solution pH was higher than pH=10. The solution was stirred for 10 minutes. Aqueous layer was separated from the mixture and the organic layer was washed with water (3×3 mL). Combine aqueous layer was dried under vacuum distillation to yield white solid (42 mg, 38%). A higher purity product was obtained by recrystallization in water to yield white solid (30 mg, 27%): HRMS (neg. ion ESI) m/z: [M-Na]$^-$ Calcd for C$_{11}$H$_{19}$BNO$_2$ 208.1509; Found 208.1513; $^1$H NMR (DMSO-d6) δ 1.35-1.84 (br. m, 12H, CH$_2$ amantadine and BH$_2$), δ 2.03 (s, 3H, CH amantadine), δ 3.46* (br. s, 2H, NH$_2$); $^{13}$C NMR (DMSO-d6) δ 28.61, δ 35.85, δ 40.24, δ 50.40; $^{11}$B NMR (DMSO-d6) δ −21.68 (br. s, 1B).

Note: *Overlap with D$_2$O solvent residual peak.

Example I—Synthesis of Amine Carboxyborane Sodium Salt

Method A:

Amine carboxyborane (5.8-8.0 mg, 26-68 mmol) was dissolved in water (500 μL). Stoichiometric amount of sodium hydroxide (15.21 M) was added to the solution of amine carboxyborane and mixed thoroughly. The solution was dried under vacuum distillation. Na—CORCB-1: $^1$H NMR (D$_2$O) δ 0.91-2.42 (br. m, 2H, BH$_2$), δ 4.72 (d, 3H, axial CH$_2$, J=12.1 Hz), δ 4.82* (d, 3H, equatorial CH$_2$, J=12.9 Hz), δ 4.98 (s, 6H, CH$_2$); $^{13}$C NMR (D$_2$O) δ 70.59, δ 75.37; $^{11}$B NMR (D$_2$O) δ −15.16 (br. m, 1B); Na—CORCB-2: $^1$H NMR (D$_2$O) δ 2.32-3.69 (br. m, 2H, BH$_2$), δ 7.88-8.00 (m, 2H, 2×CH), δ 8.35-8.46 (m, 1H, CH), δ 8.64-8.74 (m, 2H, 2×CH); $^{13}$C NMR (D$_2$O) δ 126.27, δ 141.82, δ 147.86; $^{11}$B NMR (D$_2$O) δ −11.42 (t, 1B, J=92.4 Hz). Na—CORCB-3: $^1$H NMR (D$_2$O) δ 1.45-2.70 (br. m, 2H, BH$_2$), δ 2.87 (s, 3H, CH$_3$); $^{13}$C NMR (D$_2$O) δ 51.55; $^{11}$B NMR (D$_2$O) δ −10.29 (t, 1B, J=97.7 Hz)

Note: *Overlap with D$_2$O solvent residual peak.

Method B:

Amine carboxyborane sodium salts were made during the amine exchange purification steps. After solvent was removed from the crude product, the crude product with higher percent of desired product was obtained by recrystallization in acetone and water or CORCB-3 was removed from the crude product by washing with water. The crude product was suspended in chloroform and water and pH was adjusted to higher than pH=10. Organic layer was separated out and the aqueous was wash with chloroform several times Amine carboxyborane sodium salts were recrystallized in water to yield white solid with 10-72% recovery.

Example J—Synthesis of Amine Carboxyborane Ammonium Salts

Amine carboxyborane (5.8-8.0 mg, 26-68 mmol) was dissolved in water (500 μL-2.00 mL). Stoichiometric amount of ammonium hydroxide (5.01 M) in deuterated water was added to the solution of amine carboxyborane and mixed thoroughly. The solution was dried under vacuum distillation.

NH$_4$—CORCB-1: $^1$H NMR (D$_2$O) δ 0.91-2.42 (br. m, 2H, BH$_2$), δ 4.72 (d, 3H, axial CH$_2$, J=11.8 Hz), δ 4.83* (d, 3H, equatorial CH$_2$, J=12.9 Hz), δ 4.98 (s, 6H, CH$_2$); $^{13}$C NMR (D$_2$O) δ 70.30, δ 75.28; $^{11}$B NMR (D$_2$O) δ −15.12 (br. m, 1B);

Note: *Overlap with D$_2$O solvent residual peak.

NH$_4$—CORCB-2: $^1$H NMR (D$_2$O) δ 2.35-3.67 (br. m, 2H, BH$_2$), δ 7.89-7.99 (m, 2H, 2×CH), δ 8.35-8.45 (m, 1H, CH), δ 8.63-8.74 (m, 2H, 2×CH); $^{13}$C NMR (D$_2$O) δ 126.27, δ 141.83, δ 147.87; $^{11}$B NMR (D$_2$O) δ −11.41 (t, 1B, J=96.3 Hz) NH$_4$—CORCB-3: $^1$H NMR (D$_2$O) δ 1.45-2.69 (br. m, 2H, BH$_2$), δ 2.86 (s, 3H, CH$_3$); $^{13}$C NMR (D$_2$O) δ 51.55; $^{11}$B NMR (D$_2$O) δ −10.28 (t, 1B, J=97.7 Hz) NH$_4$—CORCB-4: $^1$H NMR (D$_2$O) δ 1.01 (s, 6H, CH$_3$), δ 1.20-2.45 (br. m, 15H, memantine and BH$_2$); $^{11}$B NMR (D$_2$O) δ −21.35 (br. s, 1B)

Example K—Synthesis of Hexamethylenetetramine Carboacetaminophenborane (CORCB-1-TY)

Hexamethylenetetramine carboacetaminophenborane (CORCB-1-TY) was prepared as follows. Trimethylamine carboacetaminophenborane (CORCB-3-TY) (73 mg, 0.29 mmol) and hexamethylenetetramine (84 mg, 0.58 mmol)

were dissolved or suspended in THF or toluene (8.0 mL), protected from the atmosphere by purging with $N_2$ gas, and maintained at 25-67° C. for 24 hours. The solution was purged with $N_2$ gas for 5 minutes and concentrated by vacuum distillation leaving white solid crude product. The residue was purified by recrystallization in dichloromethane and hexane to yield a white solid (18 mg, 30%)*: HRMS (pos. ion ESI) m/z: $[M+Na]^+$ Calcd for $C_{15}H_{22}BN_5O_3+Na^+$ 353.1750; Found 353.1767; $^1H$ NMR ($CDCl_3$) δ 2.15 (s, 3H, $CH_3$), δ 4.48 (d, 3H, axial $CH_2$, J=11.9 Hz), δ 4.58 (d, 3H, equatorial $CH_2$, J=12.7 Hz), δ 4.82 (s, 6H, $CH_2$), δ 6.94-7.03 (m, 2H, aromatic), δ 7.28* (s, 1H, NH), δ 7.42-7.51 (m, 2H, aromatic); $^{13}C$ NMR ($CDCl_3$) δ 24.78, δ 72.88, δ 77.43, δ 120.86, δ 123.13, δ 134.83, δ 147.87, δ 168.36; $^{11}B$ NMR ($CDCl_3$) δ −14.76 (br. s, 1B); FT-IR (solid, ATR) 1610 $cm^{-1}$ (C—C aromatic), 1660 $cm^{-1}$ (C=O), 2410 $cm^{-1}$ ($BH_2$), 3250-3380 $cm^{-1}$ (N—H).

Note: * $^1H$ NMR spectra indicated that NMR sample contained 4% of acetaminophen that was formed from decomposition of CORCB-1-TY in $CDCl_3$.
**Overlap with acetaminophen,
***Overlap with $CDCl_3$ Example L—Synthesis of Trimethylamine Carboacetaminophenborane (CORCB-3-TY)

Trimethylamine carboacetaminophenborane (CORCB-3-TY) was prepared as follows. Trimethylamine carboxyborane (351 mg, 3.0 mmol), acetaminophen (499 mg, 3.3 mmol) and N,N'-dicyclohexylcarbodiimide (1.86 g, 9.0 mmol) were dissolved in THF (17 mL), protected from the atmosphere, and maintained at 25° C. to 67° C. for 24 hours. Solid was removed by filtration. The liquid layer was cooled to 0° C. for 30 minutes and more solid was removed by filtration. Finally liquid portion was concentrated by vacuum distillation leaving white solid crude product. The solid was purified by recrystallization in dichloromethane, acetone and hexane to yield a white solid (240 mg, 32%)*: $^1H$ NMR ($CDCl_3$) δ 2.13 (s, 3H, $CH_3$ acetaminophen), δ 2.79 (s, 9H, $CH_3$), δ 6.92-7.00 (m, 2H, aromatic), δ 7.39-7.47 (m, 2H, aromatic), δ 7.54 (s, 1H, NH); $^{13}C$ NMR ($CDCl_3$) δ 24.66, δ 52.52, δ 120.96, δ 123.14, δ 134.79, δ 148.03, δ 168.55; $^{11}B$ NMR ($CDCl_3$) δ −9.46 (br. s, 1B).

Note: * $^1H$ NMR spectrum indicated that NMR sample contained 10% of acetaminophen that was formed from decomposition of CORCB-3-TY in $CDCl_3$.

Example M—Synthesis of trimethylamine carboethyl-4-aminobenzoateborane (CORCB-3-BENZ)

Trimethylamine carboethyl-4-aminobenzolateborane (CORCB-3-BENZ) was prepared as follows. Trimethylamine carboxyborane (50 mg, 0.43 mmol) and benzocaine (43 mg, 0.26 mmol) were dissolved in chloroform (1 mL), dichloromethane (1 mL) and hexane (2 mL), protected from the atmosphere by purging with $N_2$ gas, and maintained at 40° C. to 60° C. for 5 days. The solution was purged with $N_2$ gas for 5 minutes and concentrated by vacuum distillation leaving white solid crude product. The residue was purified by recrystallization in chloroform and hexane to yield a white solid (27 mg, 47%)*: HRMS (pos. ion ESI) m/z: $[M]^+$ Calcd for $C_{13}H_{21}BN_2O_3$ 264.1645; Found 264.1645; $^1H$ NMR (DMSO-d6) δ 1.30 (t, 3H, $CH_3$, J=7.1 Hz), 1.50-2.43 (br. m, 2H, $BH_2$), δ 2.71 (s, 9H, $CH_3$), δ 4.26 (q, $CH_2$, J=7.1 Hz), δ 7.76-7.85 (m, 4H, aromatic), δ 9.30 (s, 1H, NH); $^{13}C$ NMR (DMSO-d6) δ 14.26, δ 51.41, δ 60.11, δ 117.90, δ 122.14, δ 129.90, δ 144.87, δ 165.53, δ 195.76; $^{11}B$ NMR (DMSO-d6) δ −8.41 (br. s, 1B).

Note: * $^1H$ NMR spectrum indicated that NMR sample contained benzocaine that was formed from decomposition of CORCB-3-BENZ (4% in DMSO-d6 and 29% in $CDCl_3$).

CO Release Property of CORCBs Under Physiological Conditions In Vitro:
Methods for CO Measurement:
CO releasing property of CORCBs was tested by various methods each confirming CO release and the decomposition rates agreeing between the two methods: NMR spectroscopy and CO meter.

NMR Spectroscopy:
The kinetics of compound decomposition was followed by observing the ratio of the amount of free amine group to the original compound using $^1H$ NMR. For instance, Hexamethylenetetramine carboxyborane (CORCB-1) in $D_2O$ at the concentration of 12 mg/mL was incubated at 37° C. in the standard NMR tube. $^1H$ NMR spectra were obtained at different time points to study the kinetics of product formation. The appearance of a singlet peak at δ 4.84 ppm signifies HMTA group released by decomposition of CORCB-1 molecule (FIG. 1A). The ratio of integrated peaks were used for determining the percent of each species present and plotted as a function of time to show the kinetics of auto-decomposition.

$^1H$, $^{11}B$, and $^{13}C$ NMR spectra were recorded at different time points to study the kinetics as well as to observe transformation of CORCB-1 into the products. In addition to CO as the product of interest, another species produced is borate which is identified by $^{11}B$ NMR at δ 19.63 ppm (FIG. 1B). In addition to borate, $^1H$ NMR and $^{13}C$ NMR spectra identified HMTA as another product from compound decomposition (FIG. 1C). This result suggests a general decomposition route for the amine carboxyboranes producing CO, borate, and an amine group which in this case is HMTA. Being able to predict the products of decomposition gives us the ability to estimate toxicity of these compounds. Based on overall results of CO release and decomposition products, carboxyboranes can be used as a prodrug to protect the drug molecule as well as to increase the solubility which is one of the important aspects of pharmacological parameters.

Co Meter:
A test to confirm that CO is one of the decomposition products from CORCBs is done by utilizing commercially available CO meter. Four μmole of the compounds at the concentrations of 6-12 mg/mL in aqueous solution was incubated at 37° C. in a sealed vessel with 50 mL gas space. CO meter was used to read the concentration of liberated CO gas from the solution. Measurement by CO meter in ppm, after converting to the micromole amount, was used for calculating the percent CO released based on the original amount of compound.

Myoglobin Assay:
Since there was no literature that reported the use of CO meter with CO releasing molecules, to further confirm that CORCBs release CO, Mb assay was performed using the standard procedure used with other CO releasing compounds. In brief, 1 mM horse Mb in 50 mM sodium phosphate buffer (pH 7.4) was deoxygenated using 3 equivalents of sodium dithionite. Excess dithionite was removed by desalting column. Deoxy-Mb at the concentration of 69 μM was mixed with CORM (50× excess) and incubated in 37° C. Visible spectra in the range of 550-600 nm were recorded at every 10 minutes. Overlaid spectra of these samples show a gradual transformation of deoxy-Mb to carboxy-Mb (FIG. 2). The percent CO released calculated was approximately 1% in one hour.

Example 1

In order to determine whether CO is produced in physiological condition, CORCB acid forms were dissolved in aqueous solution at neutral pH. The solution was then subjected to incubation at 37° C. for extended period of time. For studies using NMR, CORCBs were dissolved in $D_2O$. The kinetics of CORCB molecules breaking down to produce CO is determined by taking $^1H$ NMR spectra at various time points (FIG. 3). The rates are generally constant over a long period of time. The rate of decomposition of CORCB-1 is constant in the beginning at 0.85% per hour but it decreases slightly after one day. CORCB-2, CORCB-3, and CORCB-5 have much slower CO release rates than CORCB-1 which has a half-life of 3.5 days. CORB-1-TY, acetaminophen ester of CORCB-1, decomposes to completion in 12 days. CORCB-4 and CORCB-6 acid forms have low solubility in water; hence, they were not tested for auto-decomposition.

Example 2

CORCB sodium and ammonium salts were also tested for decomposition by using $^1H$ NMR spectroscopy. Samples were set up as in Example 1 and rate of decomposition measured (FIG. 4). Both sodium and ammonium salts give similar results as the acid forms with CORCB-1 having the highest rate of decomposition.

The sodium and ammonium salts of CORCB-4 were soluble in water. Results from $^1H$, $^{11}B$, and $^{13}C$ NMR spectra showed that sodium salt of CORCB-4 does not decompose in measurable amount but ammonium salt slowly decomposes to about 13% in 12 days as seen in FIG. 4B. This, in comparison to ammonium salt of CORCB-2, is higher auto-decomposition rate but not very significant compared to that of CORCB-1 ammonium salt. The $^1H$ NMR of CORCB sodium salts suggest that very little auto-decomposition occur for most of the carboxyboranes except Na—CORCB-1 which had 33.1% decomposed within 24 hours (FIG. 4A).

Example 3

Although NMR spectroscopy can suggest the decomposition of CORCB molecules, it does not detect CO molecule in the sample. CO liberated from the molecules and coming out to the head space are detected and quantified by using CO meter. FIG. 5 compares amount of CO released by CORCBs incubated for 24 hours at 37° C. CORCB-5 releases CO at a much slower rate than the others while CO formed from CORCB-3 is negligible. At 24 hour, CORCB-5 had 0.86% CO liberated which is very similar to the 1.0% from $^1H$ NMR analysis. Acetaminophen ester of CORCB-1 (CORCB-1-TY) shows a much higher decomposition rate (11.3% $^1H$ NMR, 12.3% CO meter) than the other CORCB s but lower than its original counterpart, CORCB-1. CO release rate is approximately 1% per hour in the physiological temperature of 37° C. for CORCB-1, consistent with the $^1H$ NMR result. Sodium salts of CORCBs 1-6 were also tested for the CO releasing property (FIG. 6). Sodium salt of CORCB-1 provides higher amount of CO (33%) in 24 hours compared to 23% for the acid form. The CO release rates in other CORCB sodium salts remain the same as in the protonated acid form which are essentially close to zero.

Generating CO in the Presence of Reactive Oxygen Species (ROS):

Example 4

All amine carboxyboranes express a faster CO release rate when incubated with the reactive oxygen species. The two tested are the common ROS formed naturally in the cells—a non-radical hydrogen peroxide ($H_2O_2$) and Fenton reagent which is a more reactive hydroxyl radical (.OH) formed from $Fe^{2+}$ and $H_2O_2$. Four µmole of CORCB compounds were mixed in an aqueous solution with ROS and incubated in a sealed vessel. At respective times, the head space air was injected into the meter to read the amount of CO produced. For analysis by NMR spectroscopy, the reaction mixture was prepared in NMR tube in $D_2O$ solvent and incubated for the amount of time indicated. A comparison of the CO release rates are summarized in the following tables. While some CORCBs have increased amount of CO produced when treated with 3 times equivalents of $H_2O_2$, CORCB-1 produces similar or less amount of CO. In every sample, either acid or salt form, the hydroxyl radical extracts the amount of CO to a much higher magnitude within a very short amount of time. This suggests that the mechanism of CO release is different based on the surrounding condition, and a radical ROS would act much faster than a non-radical ROS in releasing CO.

TABLE 1

Rate of % CO released by CORCBs per †24 hour and ‡5 minutes

| Compound | †Autodecomposition | †With $H_2O_2$ | ‡With Fenton Reagent |
|---|---|---|---|
| CORCB-1 | 23.47 ± 0.38 | 20.86 ± 0.82 | 60.90 ± 0.52 |
| CORCB-2 | 2.99 ± 0.06 | 20.22 ± 0.35 | 72.64 ± 2.57 |
| CORCB-3 | 0.13 ± 0.01 | 18.73 ± 0.24 | 76.64 ± 1.33 |

TABLE 2

Rate of % CO released by CORCB sodium salts per †24 hour and ‡5 minutes

| Compound | †Autodecomposition | †With $H_2O_2$ | ‡With Fenton Reagent |
|---|---|---|---|
| CORCB-1 salt | 33.12 ± 0.33 | 11.99 ± 0.19 | 41.61 ± 0.57 |
| CORCB-2 salt | 0.36 ± 0.13 | 12.66 ± 0.21 | 43.46 ± 0.73 |
| CORCB-3 salt | 0.14 ± 0.02 | 7.41 ± 0.16 | 33.46 ± 0.90 |

Example 5

The reaction with $H_2O_2$ is slow-acting, therefore, NMR spectroscopy can be used for monitoring the rate. On the other hand, the radical specie (Fenton reagent) acts immediately making it difficult to monitor with NMR spectroscopy. $^1H$ NMR spectra show that all CORCBs decompose to individual amine groups when 1.5 equivalents of $H_2O_2$ was added (FIG. 7). The most reactive one is Na—CORCB-4 which goes to almost completion (96.4%) within 24 hours. This is unexpected as CORCB-1 has always been the one to decompose at a fastest rate. CORCB-3 measurement was discontinued after 24 hours because trimethylamine evaporates and leaves the solution as it is being formed causing unreliable integration of the peaks for calculation. The key finding here is that the breakdown of CORCB molecules by $H_2O_2$ releases amine groups attached to the carboxyborane but does not necessarily produce CO. As seen in FIG. 8, comparison of $^1H$ NMR and meter readings shows a drastic difference between the two methods when CORCBs encounter ROS. The CO measurements read by CO meter for these same samples (FIG. 8) do not provide high amount of CO giving unmatched results between $^1H$ NMR and CO meter. CORCB-1 analyzed by $^1H$ NMR integration shows 51% of free HMTA released into the solution at 24 hours but CO meter reading gives only 12% of CO produced. While Na—CORCB-4 decomposition calculated from $^1H$ NMR is close to 100% in 24 hours, the reading from CO meter shows 1.6% only. Similar trend can also be seen for other CORCBs. This suggests that auto-decomposition of CORCBs goes through a mechanism that releases CO and amine group at the same time while $H_2O_2$ directs the mechanism mainly focusing on releasing the amine group or the drug molecules in the case of CORCB-1, CORCB-4, and CORCB-6. CO releasing and drug releasing properties of CORCBs are different depending on a specific formula in the presence of ROS. In another light, this suggests that drug molecules can be protected until they reach to the area with high level of ROS or diseased cells and can be released out quickly when they meet ROS.

Example 6

Another experiment was performed using higher amount of $H_2O_2$ to see its effect on the drug release rate, and it was found that decomposition happened too quickly (within a few minutes) and only the drug molecule in the reaction mixture was detected by the time NMR analysis was acquired. Therefore, it is appropriate to assume that the greater the amount of ROS present, the faster the drug will be released.

Increased amount of ROS not only increases the rate of drug molecule release, it also boosts the percent of CO produced. As seen on FIG. 9, the amount of CO produced is low for all the CORCBs when 1.5 equivalents of $H_2O_2$ is present. Doubling the amount to 3 equivalents substantially increases the amount of CO released. Even CORCB-2 and CORCB-3 that usually do not show much of CO releasing property give out about 10 percent of CO suggesting that ROS can positively affect the property of CORCBs. The data is summarized in Table 3.

TABLE 3

Summary of decomposition rates/CO release rates at 24 hours measured by $^1H$ NMR and CO meter

|  | Samples | $^1H$ NMR | Meter |
|---|---|---|---|
| Autodecomposition | CORCB-1 | 19% | 24% |
|  | CORCB-2 | 0.40% | 3% |
|  | CORCB-3 | not measurable | not measurable |
|  | CORCB-4 | not soluble | not soluble |
|  | CORCB-5 | 1% | 0.86% |
|  | CORCB-1-TY | 11.30% | 12.30% |
|  | Na-CORCB-1 | 33.20% | 33.10% |
|  | Na-CORCB-2 | 0.46% | 0.36% |
|  | Na-CORCB-3 | not measurable | not measurable |
|  | Na-CORCB-4 | not measurable | 0.06% |
|  | Na-CORCB-6 | not measurable | 0.16% |
|  | $NH_4$-CORCB-1 | 26.40% | 28.70% |
|  | $NH_4$-CORCB-2 | 0.03% | not measurable |
|  | $NH_4$-CORCB-3 | not measurable | not measurable |
|  | $NH_4$-CORCB-4 | 12.80% | not soluble |

TABLE 3-continued

Summary of decomposition rates/CO release rates at 24 hours measured by $^1H$ NMR and CO meter

|  | Samples | $^1H$ NMR | Meter |
|---|---|---|---|
| With 1.5x $H_2O_2$ | CORCB-1 | 50.90% | 12.10% |
|  | CORCB-2 | 37.50% | 1.00% |
|  | CORCB-3 | 44.50% | 2.70% |
|  | Na-CORCB-4 | 96.40% | 1.60% |
|  | CORCB-5 | 35.90% | 0.50% |
|  | Na-CORCB-6 | 36.90% | 0.80% |

Example 7

CO releasing property of CORCBs is not limited only to the neutral environment. It works in any pH ranging from 2 to 12 as evident in FIG. 10. In fact, CO release rate is the lowest in pH 7 but higher as the pH shifts to extreme acidic or basic conditions. CO is released at the highest amount in the acidic condition of pH 2 with more than 25% in 12 hours.

Study of CO Effect In Vitro

Example 8: Inhibition of LPS-Induced TNF-α Production by CORCBs

It is commonly known that lipopolysaccharide (LPS), a cytotoxin produced from *E. coli*, induces inflammatory factors in mammalian cells. To test the anti-inflammatory effect of CORCBs, mouse macrophage cells (RAW264.7) were used. $2\times10^4$ cells per well was seeded in 96-well plate with different concentrations of CORCBs. Cells were incubated in DMEM with 10% FBS at 37° C. and 5% $CO_2$ for 24 hours. LPS (100 ng/mL) was then added and incubated for 4 additional hours. The media containing secreted inflammatory cytokines were collected and these cells were subjected to cell viability test to check their viability. TNF-α concentration in each sample was measured by ELISA assay.

After normalizing TNF-α concentration and cell viability against LPS induced and untreated cells regarded as 100%, the results were compared in FIGS. 11 and 13 for CORCB-1 and CORCB-3, respectively. As seen on FIG. 11, increasing concentration of CORCB-1 leads to lower TNF-α concentration which suggests that CORCB-1 inhibits the production of TNF-α. Based on the cell viability test performed, all cells were still healthy after the tests confirming that reduction of TNF-α concentration is resulted exclusively from CORCB-1, not from lower amount of cells.

CORCB-3 was also tested for the TNF-α assay. Since CORCB-3 does not readily decompose to produce CO in the ordinary cellular condition, the anti-inflammatory effect of CO is not as remarkable as that of CORCB-1. Cells treated with different concentrations of CORCB-3 show similar amounts of TNF-α produced as in the untreated cells (FIG. 13). Regardless of the amount of TNF-α, all cells remain viable suggesting that CORCB molecules are not toxic to the cells but CO may not always be produced depending on a specific CORCB formula.

Example 9: Toxicity of CORCB-1 In Vitro

Cytotoxicity of CORCBs was tested with RAW264.7 cells using Cell Titer Blue assay. In brief, cells were seeded at the density of $2\times10^4$ cells per well in 96-well plate with different concentrations of CORCBs. Cells were incubated in DMEM with 10% FBS at 37° C. and 5% $CO_2$ for 24 hours. Cell Titer Blue reagent was added into the wells and incubated for 4 more hours in the normal cell growth conditions. The fluorescence signal of the converted reagent resulted from the viable cells was measured.

The signals from various samples were normalized against untreated cells. A concentration range of 0.5-10 mM CORCB-1 was tested for toxicity. As shown in FIG. 12, none of the concentration shows adverse effect on cell viability. In fact, all cells treated with CORCB-1 show higher growth than untreated cells. The control cells that are treated with 1 mM $H_2O_2$ show 44% viability after 24 hours. During the CO release process, the amine group, hexamethylenetetramine (HMTA) in this case, gets detached from CORCB-1 molecule. In order to see that if there is any toxicity from HMTA itself, a few controls with varying concentration of HMTA were included in the test. These controls show a certain extent of toxicity by HMTA with most cells losing viability at 2 mM concentration. Although CORCB-1 produces HMTA in the process of releasing CO, the cells are protected from the cytotoxic effect of HMTA in the CORCB-1 samples.

FIG. 14 shows the cytotoxicity test for CORCB-3. Similar to CORCB-1, up to 10 mM concentration of the compound were tested for cellular toxicity. Since the byproduct, trimethylamine, is a volatile compound, the effect of it alone was not tested. The results show that all cells are still viable and growing at the same rate as untreated cells suggesting CORCB-3 is not toxic at the levels tested.

Example 10: Faster CO Release Rate of CORCBs with ROS

CORCBs were tested together with an oxidant, hydrogen peroxide ($H_2O_2$), for a faster anti-inflammatory effect. RAW264.7 cells at the density of $2 \times 10^4$ cells per well in 96-well plate were treated with varying concentrations of CORCB plus different concentrations of $H_2O_2$. As seen on FIGS. 15 and 16, CORCBs release CO readily in the presence of reactive oxygen species, $H_2O_2$ in this case, and lower the amount of TNF-α produced even further. At 1 mM concentration, CORCB-1 alone lowers the amount of TNF-α secreted to about 80% but together with $H_2O_2$ does so to about 25% (FIG. 15). The rate of auto-decomposition of CORCB-1 and CORCB-3 are around 20% and 3% per day, respectively. However, the presence of ROS causes CO production much faster and therefore, the effects together with ROS seen on FIGS. 15 and 16 are much more profound. This is consistent with the in vitro CO release data from previous examples that reactive oxygen species (ROS) accelerate the CO production process from CORCB molecules. Cell viability test done on the same cells after the TNF-α assay shows that the cells are still viable. This suggests that CORCBs are able to use reactive oxygen species (ROS) to promote faster CO release. In addition, our results (data not shown) demonstrate that cell survival rate, in the presence of 1 mM $H_2O_2$, is raised significantly when CORCBs are added in the culture. This may be in part due to the unknown mechanism influenced by CO. Nevertheless, this shows that CORCBs can rescue cells from oxidative damage caused by ROS.

Example 11: Promotion of Cell Growth and Anti-Tumor Activity

Using mouse macrophage cells, as discussed in Example 8, it was found that CORCB-1 promotes cell growth since the percentage of viable cells is always more than that of untreated cells.

Therefore, further test was to determine if CORCBs can do the same when the cells are under stressed condition. This is done by using human cell lines—fibroblast tumor cells (Hs 895.T) and normal fibroblast cells (Hs 895.Sk). Cells were seeded at the density of $3 \times 10^3$ cells per well in 96-well plate with different concentrations of CORCBs in DMEM media without FBS, and incubated at 37° C. with 5% $CO_2$ for 2 days. When the cells were given minimal nutrients, their growth rate slows down. However, as shown in FIG. 17, CORCB-1 can promote cell growth resulting in higher percent survival compared to the hydrogen peroxide treated cells and HMTA treated cells. Comparison with untreated cells shows that the more CORCB-1 in the media leads to the higher number of viable cells with close to 180% within 48 hours. In addition, the growth stimulation by CORCB-1 is more selective towards the normal fibroblast cells while the tumor cells growth rate lags behind. This effect is again presented in FIG. 18 with CORCB-6 sodium salt. As seen in FIG. 17 with HMTA, the free drug (Amantadine) destroys the cells at 1 mM concentration in this condition leaving only about 20%. Cell viability with CORCB-6 is lower than CORCB-1 but at 2 mM concentration, the selectivity can be seen much better with lowering of the tumor cell survival while increasing the percent viability of normal fibroblast cells.

To further test the anti-tumor effect of CORCBs in the presence of ROS, fibroblast tumor cells (Hs 895.T) and normal fibroblast cells (Hs 895.Sk) were incubated with 1 mM of CORCB-1 and 0.2 mM of $H_2O_2$ mixed in the DMEM media without FBS. Media was exchanged every 2 days for longer incubation periods such as 4 and 6 days. FIG. 19 shows the percent viable cells as a function of time. Both tumor and normal cells are close to 100% viable at 2 days, but for longer treatment periods, tumor cells growth rate declines and normal cell growth remains steady. By $6^{th}$ day, % viability of tumor cells is down to 47% and normal cell growth is still at 89% suggesting that CORCBs can be used in treatment of cancer cells in combination with ROS. Normal cells are preserved under stressed condition while tumor cells are destroyed.

It was found that CORCBs can rescue the cells from damages caused by other toxic agents. This was tested by using a chemotherapy drug, imatinib, in normal human skin fibroblast cells (Hs 895.Sk). The cultures were treated with 20 μM and 40 μM concentration of imatinib as controls to see their toxicity. Samples with mixtures of CORCB-1 and imatinib were also incubated and cell viability was determined on 2, 4, and 6 days. Media was exchanged every 2 days with fresh reagents. Summary of the results is presented in FIG. 20. Cells treated with 40 μM imatinib lose their viability at 4 days and the ones treated with 20 μM are killed by 6 days. Important discovery here is that the cells treated with a mixture of imatinib and CORCB-1 show high viability with around 70% survival rate on day 4 and 6 suggesting that CORCBs can be used for rescuing damaged cells or in combination with chemotherapy drugs to prevent damages to the normal cells.

The above preferred embodiments and examples were given to illustrate the scope and spirit of the present invention. These embodiments and examples will make apparent to those skilled in the art of other embodiments and examples. The other embodiments and examples are within the contemplation of the present invention. Therefore, the present invention should be limited only by the amended claims.

What is claimed is:

1. A compound of the formula

XBY1Y2C(O)V                                    I or pharmaceutically acceptable salts,
where
each of Y1 and Y2 is H;
V is O⁻, OR1 or NR1R2 or is a first drug, which drug has an amino function or an alcohol moiety thereon in which a hydrogen atom of the alcohol or amine is not present;
R1 and R2 are independently hydrogen, lower alkyl, aryl, aryl lower alkyl, cycloalkyl, cycloalkyl lower alkyl or Ar—N(R3)C(O)R4 or is a first drug, which drug has an amino function or an alcohol moiety thereon in which a hydrogen atom of the alcohol or amine is not present;
Ar is aryl;
each R3 and R4 are independently hydrogen or lower alkyl;
X is a second drug selected from Hexamethylenetetramine, Memantine, Amantadine, Aripiprazole, Rosuvastatin, Pregabalin, Scopolamine, Sitagliptin, Glatiramer acetate, Abacavir, Abiraterone, Amlodipine, Amphetamine, Anastrozole, Atazanavir, Atomoxetine, Azacitidine, Bendamustine, Bortezomib, Buprenorphine, Celecoxib, Cinacalcet, Ciprofloxacin, Clopidogrel, Dabigatran, Dacarbazine, Darunavir, Dasatinib, Desvenlafaxine, Dexlansoprazole, Dexmethylphenidate, Dipyridamole, Duloxetine, Emtricitabine, Epinephrine, Erlotinib, Escitalopram, Esomeprazole, Eszopiclone, Fentanyl, Fingolimod, Formoterol, Guanfacine, Hydrocodone, Imatinib, Imiquimod, Lamivudine, Lenalidomide, Levothryoxine, Lidocaine, Linezolid, Lisdexamfetamine, Mesalazine, Metformin, Methylphenidate, Metoprolol, Minocycline, Naloxone, Nebivolol, Niacin, Nilotinib, Octreotide Acetate, Olanzapine, Olmesartan, Oseltamivir, Oxycodone, Oxymorphone, Paliperidone, Palonosetron, Pemetrexed, Pioglitazone, Piperacillin, Prasugrel, Quetiapine, Rabeprazole, Raloxifene, Raltegravir, Ranolazine, Regadenoson, Rifaximin, Rilpivirine, Risedronic Acid, Risperidone, Ritonavir, Rivastigmine, Rizatriptan, Salbutamol, Salmeterol, Saxagliptin, Sevelamer, Sildenafil, Solifenacin, Sunitinib, Tazobactam, Telaprevir, Temozolomide, Tenofovir, ThioTEPA, Tolterodine, Valganciclovir, Valsartan, Varenicline, Vismodegib, Ziprasidone, or Zoledronic Acid, or a pharmaceutically acceptable salt thereof;
wherein R1, R2, R3, and R4 groups being independently unsubstituted or substituted with lower alkyl, halo, lower alkoxy, heterocyclic, cycloalkyl, nitro, carboxy, carbalkoxy, C(O)NR8R9, C(O)R8, or OC(O)R8, where R8 and R9 are independently hydrogen or lower alkyl.

2. The compound according to claim 1, wherein V is O⁻, OH or is a first drug, which drug has an amino function or an alcohol moiety thereon in which a hydrogen atom of the alcohol or amine function of said drug is not present or a pharmaceutically acceptable salt thereof.

3. The compound according to claim 1, wherein V is a drug containing a hydroxy group, or an amino group less a hydrogen atom on the hydroxy group or amino group or pharmaceutically acceptable salt of said drug.

4. A pharmaceutical composition comprising a therapeutically effective amount of a compound according to claim 1 and a pharmaceutically acceptable carrier therefor.

5. The compound according to claim 1, wherein V is a first drug, which drug has an amino function or an alcohol moiety thereon in which a hydrogen atom of the alcohol or amine function of said drug is not present or a pharmaceutically acceptable salt thereof.

6. The compound according to claim 1, wherein the second drug is Hexamethylenetetramine.

7. The compound according to claim 1, wherein the first drug is Acetaminophen, Rosuvastatin, Scopolamine, Glatiramer acetate, Abacavir, Abiraterone, Atorvastatin, Azacitidine, Beclomethasone Dipropionate, Bimatoprost, Budesonide, Buprenorphine, Darunavir, Dasatinib, Desvenlafaxine, Dipyridamole, Emtricitabine, Enoxaparin, Epinephrine, Ethinyl Estradiol, Etonogestrel, Everolimus, Ezetimibe, Fingolimod, Formoterol, Lamivudine, Levothyroxine, Mesalazine, Metoprolol, Minocycline, Naloxone, Nebivolol, Norgestimate, Octreotide Acetate, Olmesartan, Oxycodone, Oxymorphone, Paliperidone, Quetiapine, Raloxifine, Ranolazine, Regadenoson, Rifaximin, Salbutamol, Salmeterol, Saxagliptin, Sevelamer, Solifenacin, Tacrolimus, Testosterone, Tolterodine, Travoprost, Benzocaine, Pregabalin, Sitagliptin, Amlodipine, Amphetamine, Atomoxetine, Cinacalcet, Erlotinib, Guanfacine, Imiquimod, Lisdexamfetamine, Metformin, Methylphenidate, Oseltamivir, Pemetrexed, Valganciclovir, or Varenicline, or a pharmaceutically acceptable salt thereof.

8. The compound according to claim 1, wherein V is Acetaminophen.

9. The compound according to claim 1, wherein the compound is selected from:

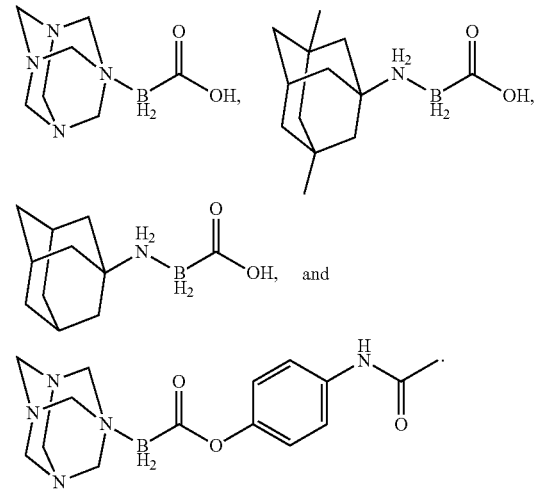

10. The compound according to claim 1, wherein the compound is:

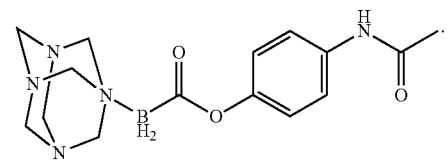

11. A compound of the formula

XBY1Y2C(O)V                                    I or pharmaceutically acceptable salts,
where
each of Y1 and Y2 is H;

V is a first drug, which drug has an amino function or an alcohol moiety thereon in which a hydrogen atom of the alcohol or amine is not present, wherein the first drug is Acetaminophen;

R1 and R2 are independently hydrogen, lower alkyl, aryl, aryl lower alkyl, cycloalkyl, cycloalkyl lower alkyl or Ar—N(R3)C(O)R4 or is a first drug, which drug has an amino function or an alcohol moiety thereon in which a hydrogen atom of the alcohol or amine is not present;

Ar is aryl;

each R3 and R4 are independently hydrogen or lower alkyl;

X is a second drug, which drug contains an amino group or X is a nitrogen containing vitamin, an amino acid, a nucleotide, or X is N(R5)(R6)(R7) or a nitrogen containing heterocyclic ring containing 1, 2, 3 or 4 nitrogen atoms, wherein one nitrogen atom is bonded directly to the boron atom, said nitrogen atom being bonded directly to the boron atom being tetravalent;

R5, R6 and R7 are independently hydrogen, lower alkyl, cycloalkyl, cycloalkyl lower alkyl, aryl, aryl lower alkyl or heterocyclic or heterocyclic lower alkyl;

wherein, aryl, heterocyclic, cycloalkyl, R1, R2, R3, R4, R5, R6, R7, R8, and R9 groups being independently unsubstituted or substituted with lower alkyl, halo, lower alkoxy, heterocyclic, cycloalkyl, nitro, carboxy, carbalkoxy, C(O)NR8R9, C(O)R8, or OC(O)R8, where R8 and R9 are independently hydrogen or lower alkyl, provided that X is not ammonia, NH(CH$_3$)$_2$, N(CH$_3$)$_3$, or nicotine, and further provided that either X is a drug or V is a drug having an amino or hydroxy group less a hydrogen atom on the amino or hydroxy group.

12. The compound according to claim 11, wherein X is a second drug.

13. A compound of the formula

XBY1Y2C(O)V    I or pharmaceutically acceptable salts, where each of Y1 and Y2 is H;

V is O⁻, OR1 or NR1R2 or is a first drug, which drug is Acetaminophen, Rosuvastatin, Scopolamine, Glatiramer acetate, Abacavir, Abiraterone, Atorvastatin, Azacitidine, Beclomethasone Dipropionate, Bimatoprost, Budesonide, Buprenorphine, Darunavir, Dasatinib, Desvenlafaxine, Dipyridamole, Emtricitabine, Enoxaparin, Epinephrine, Ethinyl Estradiol, Etonogestrel, Everolimus, Ezetimibe, Fingolimod, Formoterol, Lamivudine, Levothyroxine, Mesalazine, Metoprolol, Minocycline, Naloxone, Nebivolol, Norgestimate, Octreotide Acetate, Olmesartan, Oxycodone, Oxymorphone, Paliperidone, Quetiapine, Raloxifene, Ranolazine, Regadenoson, Rifaximin, Salbutamol, Salmeterol, Saxagliptin, Sevelamer, Solifenacin, Tacrolimus, Testosterone, Tolterodine, Travoprost, Benzocaine, Pregabalin, Sitagliptin, Amlodipine, Amphetamine, Atomoxetine, Cinacalcet, Erlotinib, Guanfacine, Imiquimod, Lisdexamfetamine, Metformin, Methylphenidate, Oseltamivir, Pemetrexed, Valganciclovir, or Varenicline, or a pharmaceutically acceptable salt thereof;

R1 and R2 are independently hydrogen, lower alkyl, aryl, aryl lower alkyl, cycloalkyl, cycloalkyl lower alkyl or Ar—N(R3)C(O)R4 or is a first drug, which drug has an amino function or an alcohol moiety thereon in which a hydrogen atom of the alcohol or amine is not present;

Ar is aryl;

each R3 and R4 are independently hydrogen or lower alkyl;

X is a second drug, which drug is Hexamethylenetetramine, Memantine, Amantadine, Aripiprazole, Rosuvastatin, Pregabalin, Scopolamine, Sitagliptin, Glatiramer acetate, Abacavir, Abiraterone, Amlodipine, Amphetamine, Anastrozole, Atazanavir, Atomoxetine, Azacitidine, Bendamustine, Bortezomib, Buprenorphine, Celecoxib, Cinacalcet, Ciprofloxacin, Clopidogrel, Dabigatran, Dacarbazine, Darunavir, Dasatinib, Desvenlafaxine, Dexlansoprazole, Dexmethylphenidate, Dipyridamole, Duloxetine, Emtricitabine, Epinephrine, Erlotinib, Escitalopram, Esomeprazole, Eszopiclone, Fentanyl, Fingolimod, Formoterol, Guanfacine, Hydrocodone, Imatinib, Imiquimod, Lamivudine, Lenalidomide, Levothryoxine, Lidocaine, Linezolid, Lisdexamfetamine, Mesalazine, Metformin, Methylphenidate, Metoprolol, Minocycline, Naloxone, Nebivolol, Niacin, Nilotinib, Octreotide Acetate, Olanzapine, Olmesartan, Oseltamivir, Oxycodone, Oxymorphone, Paliperidone, Palonosetron, Pemetrexed, Pioglitazone, Piperacillin, Prasugrel, Quetiapine, Rabeprazole, Raloxifene, Raltegravir, Ranolazine, Regadenoson, Rifaximin, Rilpivirine, Risedronic Acid, Risperidone, Ritonavir, Rivastigmine, Rizatriptan, Salbutamol, Salmeterol, Saxagliptin, Sevelamer, Sildenafil, Solifenacin, Sunitinib, Tazobactam, Telaprevir, Temozolomide, Tenofovir, ThioTEPA, Tolterodine, Valganciclovir, Valsartan, Varenicline, Vismodegib, Ziprasidone, or Zoledronic Acid, or a pharmaceutically acceptable salt thereof, or X is a nitrogen containing vitamin, an amino acid, a nucleotide, or X is N(R5)(R6)(R7) or a nitrogen containing heterocyclic ring containing 1, 2, 3 or 4 nitrogen atoms, wherein one nitrogen atom is bonded directly to the boron atom, said nitrogen atom being bonded directly to the boron atom being tetravalent;

R5, R6 and R7 are independently hydrogen, lower alkyl, cycloalkyl, cycloalkyl lower alkyl, aryl, aryl lower alkyl or heterocyclic or heterocyclic lower alkyl;

wherein, aryl, heterocyclic, cycloalkyl, R1, R2, R3, R4, R5, R6, R7, R8, and R9 groups being independently unsubstituted or substituted with lower alkyl, halo, lower alkoxy, heterocyclic, cycloalkyl, nitro, carboxy, carbalkoxy, C(O)NR8R9, C(O)R8, or OC(O)R8, where R8 and R9 are independently hydrogen or lower alkyl, provided that X is not ammonia, NH(CH$_3$)$_2$, N(CH$_3$)$_3$, or nicotine when V is OH or O⁻, and further provided that either X is a drug or V is a drug having an amino or hydroxy group less a hydrogen atom on the amino or hydroxy group.

14. The compound according to claim 13, wherein V is a first drug.

15. The compound according to claim 13, wherein V is Acetaminophen.

16. The compound according to claim 13, wherein X is Hexamethylenetetramine.

17. The compound according to claim 13, wherein the compound is selected from:

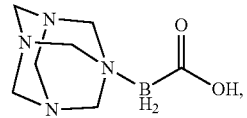

-continued
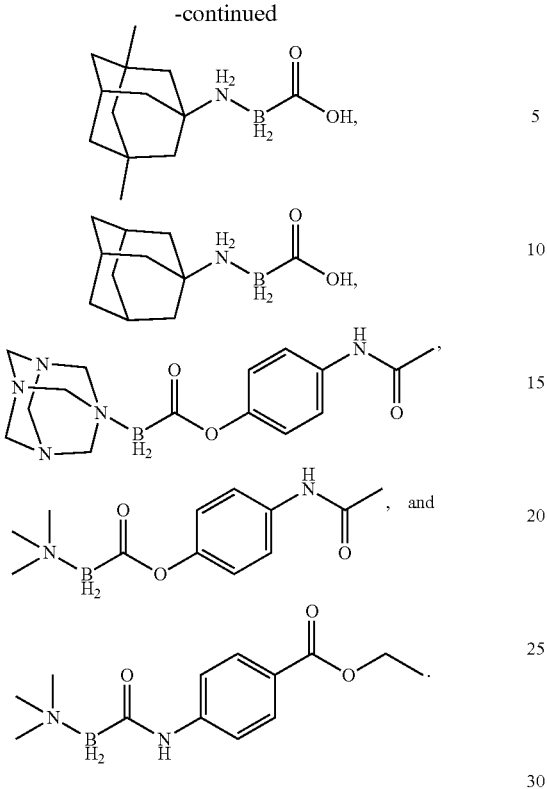
* * * * *